(12) United States Patent
Yanase et al.

(10) Patent No.: US 6,187,872 B1
(45) Date of Patent: *Feb. 13, 2001

(54) WATER-ABSORBENT AGENT AND METHOD FOR MANUFACTURING THE SAME

(75) Inventors: Toru Yanase, Ibo-gun; Kazuki Kimura, Himeji; Shin-ichi Fujino, Himeji; Kinya Nagasuna, Himeji; Kunihiko Ishizaki, Suita; Hirotama Fujimaru, Himeji; Nobuyuki Harada, Suita, all of (JP)

(73) Assignee: Nippon Shokubai Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/051,313

(22) PCT Filed: Aug. 5, 1997

(86) PCT No.: PCT/JP97/02706

§ 371 Date: Apr. 6, 1998

§ 102(e) Date: Apr. 6, 1998

(87) PCT Pub. No.: WO98/05420

PCT Pub. Date: Feb. 12, 1998

(30) Foreign Application Priority Data

Aug. 7, 1996  (JP) .................................................... 8-208622

(51) Int. Cl.[7] ................................ C08F 8/12; C08F 2/00; C08F 30/04

(52) U.S. Cl. ........................ 525/330.2; 526/88; 526/240

(58) Field of Search ........................... 525/330.2; 526/88, 526/240

(56) References Cited

U.S. PATENT DOCUMENTS

| | | | |
|---|---|---|---|
| 4,295,987 | * 10/1981 | Parks | 252/194 |
| 4,340,706 | * 7/1982 | Obayashi et al. | 526/207 |
| 4,654,039 | * 3/1987 | Brandt et al. | 604/368 |
| 4,910,250 | * 3/1990 | Saotome | 524/556 |

(List continued on next page.)

FOREIGN PATENT DOCUMENTS

| | | |
|---|---|---|
| 57-73007 | * 5/1982 | (JP) . |
| 57-80403 | * 5/1982 | (JP) . |
| 1-103606 | * 4/1989 | (JP) . |
| 5-156034 | * 6/1993 | (JP) . |
| 6-184212 | * 7/1994 | (JP) . |
| 97/06190 | * 2/1987 | (WO) . |

*Primary Examiner*—David W. Wu
*Assistant Examiner*—Tanya Zalukaeva
(74) *Attorney, Agent, or Firm*—Nixon & Vanderhye

(57) ABSTRACT

A hydrogel polymer obtained by polymerizing a monomer component including acrylic acid (salt) is post-neutralized so that each of polymer particles derived from a polymer produced by neutralizing the hydrogel polymer has an allowable neutralization ratio. The polymer as obtained by neutralizing the hydrogel polymer is reacted with a crosslinking agent reactive to a functional group of the polymer. The allowable neutralization ratio, for example, is a neutralization ratio which is not lower, by not less than 20 mole percent, or more than, at least 55 mole percent, than an average neutralization ratio of a mass of the polymer particles, and the post-neutralization is carried out so that a number of polymer particles having a non-allowable neutralization ratio outside the allowable neutralization range is not more than 10 in 200 polymer particles, thus obtaining a water-absorbent agent having high absorbency under no applied pressure and high pressure wherein the amount of water soluble component is lower compared with the conventional water-absorbent agent and a change in pH of a swollen gel is small.

37 Claims, 3 Drawing Sheets

U.S. PATENT DOCUMENTS

| | | | |
|---|---|---|---|
| 4,985,514 | * | 1/1991 | Kimura et al. .......................... 526/88 |
| 5,112,902 | * | 5/1992 | Moriya et al. ........................ 524/503 |
| 5,145,906 | * | 9/1992 | Chambers et al. .................... 524/732 |
| 5,314,952 | * | 5/1994 | Choi et al. ............................ 525/119 |
| 5,326,819 | * | 7/1994 | Kanbayashi et al. ................. 525/119 |
| 5,385,983 | * | 1/1995 | Graham .............................. 525/330.1 |
| 5,633,316 | * | 5/1997 | Gartner et al. ..................... 525/54.32 |

* cited by examiner

WATER-ABSORBENT AGENT AND METHOD FOR MANUFACTURING THE SAME

FIELD OF THE INVENTION

The present invention relates to a water-absorbent agent and a manufacturing method of the same, and more particularly to a water-absorbent agent suitable for sanitary articles such as paper diapers (disposable diapers) and sanitary napkins, with a significantly improved water absorbing ability, and also relates to a manufacturing method of the same.

BACKGROUND OF THE INVENTION

In recent years, for absorption of large quantities of water, a water-absorbent agent such as water-absorbent resin has been widely adopted as one of the materials constituting sanitary articles such as paper diapers, sanitary napkins, and adult incontinence pads. Also, for absorbing and holding of water, such a water-absorbent agent (water-absorbent resin, etc.) has also been widely adopted as soil conditioners and drip sheets for food.

Examples of a conventionally known water-absorbent agent are as follows: (1) a partially neutralized and crosslinked polyacrylic acid, (2) hydrolyzed copolymer of starch-acrylonitrile, (3) neutralized graft polymer of starch-acrylic acid, (4) saponified copolymer of vinyl acetate-acrylic ester, (5) a crosslinked polymer of a hydrolyzed copolymer of acrylonitrile or a crosslinked polymer of a hydrolyzed copolymer of acrylamide, and (6) a crosslinked cation monomer, etc.

The properties which the water-absorbent resin is desired to possess, in order to be adopted as sanitary articles, include, for example, (a) high absorbency and high absorbing rate to be manifested upon contact with aqueous liquids such as body fluids, (b) liquid permeability, (c) high strength exhibited by a gel swollen with liquid, and (d) an ability to aspirate water from a substrate impregnated with aqueous liquid.

However, these properties are not necessarily proportionally related to one another such that, for example, as absorbency of water-absorbent resin increases, such properties as the liquid permeability, the gel strength, and the absorbing rate decrease. In order to improve a balance of the various water-absorbent properties of the water-absorbent resin, various techniques of crosslinking the surface region of the water-absorbent resin have been suggested.

As such techniques, the following methods in which specific compounds are adopted as a crosslinking agent are known. (a) A method using a polyhydric alcohol as a crosslinking agent (Japanese Unexamined Patent Application No. 180233/1983 (Tokukaisho 58-180233), and Japanese Unexamined Patent Application No. 16903/1986 (Tokukaisho 61-16903)), (b) a method using a polyglycidyl compound, a polyaziridine compound, a polyamine compound, and a polyisocyanate compound as a crosslinking agent (Japanese Unexamined Patent Application No. 189103/1984 (Tokukaisho 59-189103)), (c) a method using a glyoxal as a crosslinking agent (Japanese Unexamined Patent Application No. 117393/1977 (Tokukaisho 52-117393)), (d) a method using a polyvalent metal as a crosslinking agent (Japanese Unexamined Patent Application No. 136588/1976 (Tokukaisho 51-136588), Japanese Unexamined Patent Application No. 257235/1986 (Tokukaisho 61-257235) and Japanese Unexamined Patent Application No. 7745/1987 (Tokukaisho 62-7745)), (e) a method using a silane coupling agent as a crosslinking agent (Japanese Unexamined Patent Application No. 211305/1986 (Tokukaisho 61-211305), Japanese Unexamined Patent Application No. 252212/1986 (Tokukaisho 61-252212) and Japanese Unexamined Patent Application No. 264006/1986 (Tokukaisho 61-264006)), (f) a method using an epoxy compound and a hydroxy compound as crosslinking agents (Japanese Unexamined Patent Application No. 132103/1990 (Tokukaihei 2-132103)), and (g) a method using an alkylene carbonate as a crosslinking agent (DE-4020780, and U.S. Pat. No. 5,409,771).

Also, as a technique of uniformly carrying out surface crosslinkage in which a crosslinking agent is uniformly spread over the surface of the water-absorbent resin during a crosslinkage reaction, for example, the following methods, applied when adding the crosslinking agent, are known. (h) A method using an inorganic inactive powder (Japanese Unexamined Patent Application No. 163956/1985 (Tokukaisho 60-163956) and Japanese Unexamined Patent Application No. 255814/1985 (Tokukaisho 60-255814)), (i) a method using a dihydric alcohol (Japanese Unexamined Patent Application No. 292004/1989 (Tokukaihei 1-292004)), (j) a method using an ether compound (Japanese Unexamined Patent Application No. 153903/1990 (Tokukaihei 2-153903)), and (k) a method using alkylene oxide additive of a monchydric alcohol, an organic acid salt, lactam, etc. (Japanese Unexamined Patent Application No. 200046/1994 (Tokukaihei 6-200046), and EP-0555692).

With the described surface processing methods, some improvements in the balance of the various water-absorbent properties of the water-absorbent resin are attained, yet further improvements are needed to reach a desirable level. That is to say, in light of recent trend of an absorbent of thin sanitary articles containing a large amount of water-absorbent resin, considering the properties required for such water-absorbent resin, the water-absorbent resin made by the described methods has not reached a satisfactory level. Therefore, a further improvement in the quality of the water-absorbent resin is demanded.

The properties required for water-absorbent resin contained in high concentration in the absorbent are (1) high absorbency under no applied pressure and (2) water-absorbing properties, such as absorbency and liquid diffusivity under heavy load and high pressure, which are superior than that of conventional water-absorbent resin. Also, in the case where the absorbent containing in high concentration the water-absorbent resin is used for an extended period of time, a water soluble component (mainly water soluble polymer component) of the water-absorbent resin is gradually removed. This may result in lowering of diffusivity of aqueous liquid such as body fluids, and an increase in the amount of backlash of the aqueous liquid. For this reason, it is demanded to further reduce the amount of the water soluble component in the water-absorbent resin.

Incidentally, as a common manufacturing method of the water-absorbent resin, the following methods are known. (I) A method in which a monomer of acrylic acid or other compounds as a main component, which have been neutralized, are polymerized, and (II) a method (so-called a post-neutralization polymerization method) in which after polymerizing a monomer of acrylic acid or other compounds as a main component, which have not been neutralized or have been neutralized at a relatively low neutralization ratio within a predetermined range, resulting hydrogel polymer is neutralized as required. For example, the method (I) is adopted as the manufacturing method of water-absorbent resin disclosed in Japanese Unexamined Patent Application No. 126310/1989 (Tokukaihei 1-126310), and U.S. Pat. No.

4,985,518. However, in method (I), because a relatively large amount of water soluble component is present, when the water-absorbent agent is adopted in sanitary articles, there is a chance that the diffusivity of aqueous liquid such as body fluids is lowered and the amount of backlash of the aqueous liquid is increased. For this reason, the method (II) is considered to be more desirable as a manufacturing method of water-absorbent resin, and is suitably adopted as a method of reducing the water soluble component while maintaining high absorbency of the water-absorbent resin under no applied pressure.

Specifically, the following methods are known as an example of method (II). (1) A method in which after polymerizing the acrylic acid in the presence of a vinyl crosslinking agent, the acrylic acid thus polymerized is neutralized with alkali metals, and resulting water containing neutralized gel is further crosslinked by divalent metal ions (U.S. Pat. No. 4,295,987), (m) a method in which an alkali metal containing compound is added to a hydrogel polymer which has been prepared by polymerizing monomers containing a free acid group such as carboxylic acid, and at least 50 mole percent of the acid group of the hydrogel polymer are neutralized (U.S. Pat. No. 4,654,039), (n) a method in which an alkali metal containing compound is added to a hydrogel polymer which has been prepared by polymerizing a monomer containing a free acid group such as carboxylic acid using a copolymerizable crosslinking agent, and 50 mole percent to 90 mole percent of the acid group of the hydrogel polymer are neutralized, (o) a method in which an alkali metal containing compound is added to a hydrogel polymer which has been prepared by polymerizing a monomer containing an acid group such as carboxylic acid, and after neutralizing 50 mole percent to 90 mole percent of the acid group of the hydrogel polymer, the hydrogel polymer is crosslinked to a compound having at least two or more reactive groups which can undergo reaction with the acid group of the hydrogel polymer, and/or an alkali metal base of the acid group (Japanese Unexamined Patent Application No. 103606/1989 (Tokukaihei 1-103606), and Japanese Unexamined Patent Application No. 103615/1989 (Tokukaihei 1-103615), (p) a method in which a monomer component, which is a 10 mole percent to 50 mole percent neutralized acid group containing monomer, is polymerized so as to carry out neutralization further (Japanese Unexamined Patent Application No. 144404/1989 (Tokukaihei 1-144404), and U.S. Pat. No. 4,985,514), and (q) a method in which after adiabatically polymerizing, using a specific amount of 3 types of specific polymerization initializing agents, acrylic acid until the amount of residual monomers is not more than 1000 ppm, resulting polyacrylic acid is neutralized at a neutralization ratio of 50 mole percent to 100 mole percent, thereafter the hydrogel polymer is crosslinked by adding a specific amount of a crosslinking agent after neutralization, and the crosslinked hydrogel polymer is dried and pulverized (Japanese Unexamined Patent Application No. 174414/1991 (Tokukaihei 3-174414), and U.S. Pat. No. 5,145,906).

However, as a result of studying each of the described methods, the inventors of the present invention found that in the water-absorbent resin as obtained by neutralization after polymerizing acid group containing monomers as in method (II), while it was possible to reduce the water soluble component, the effect of crosslinkage was not sufficient even when the surface crosslinkage process was carried out.

Namely, specifically, in method (II), it was found that while it was possible to improve to a certain level the absorbency under applied pressure when the applied load is low (for example, 20 g/cm$^2$), it was difficult to improve absorbency under high pressure (for example, 50 g/cm$^2$). Also, even when a water-absorbent agent with high absorbency under high pressure was obtained, it was difficult to stably obtain such a water-absorbent agent. Indeed, in any of the described methods in accordance with method (II), it was difficult to stably obtain a water-absorbent agent with high absorbency under high pressure.

For this reason, there is a need for (i) a water-absorbent agent having high absorbency not only under no applied pressure but also under high pressure in which the amount of water soluble component is reduced compared with a conventional water-absorbent agent, which can be suitably adopted as a thin absorbent, as well as (ii) a method of manufacturing such a water-absorbent agent.

Also, the inventors of the present invention found after studying that, as described above, in the water-absorbent resin obtained by neutralization after polymerizing the acid group containing monomers, when the water-absorbent resin takes a form of swollen gel by absorbing an aqueous liquid, the pH in the swollen gel is changed with time. Thus, when such a water-absorbent resin is adopted in sanitary articles, there arises a problem of safety due to residual alkali used in neutralization and a problem of unstable pH in the sanitary articles. Therefore, as a water-absorbent agent which can be suitably adopted as an absorbent of sanitary articles, etc., there is a need for a water-absorbent agent whose change in pH with time is small when the water-absorbent agent takes a form of swollen gel by absorbing aqueous liquid.

DISCLOSURE OF INVENTION

The present invention is achieved in finding a solution to above mentioned problems, accordingly it is an object of the present invention to provide a water-absorbent agent having high absorbency under no applied pressure and under high pressure wherein the amount of water soluble component is lower than that of a conventional water-absorbent agent, and to provide a manufacturing method for obtaining the same. It is another object of the present invention to provide a water-absorbent agent in which a change in pH of a swollen gel is small, and a manufacturing method thereof.

Earnest researches have been made to accomplish the above objects. As a result, the inventors of the present invention have found that the amount of water soluble component can be reduced by post-neutralizing a hydrogel polymer obtained by polymerizing a monomer component including an acid group containing unsaturated monomer (salt), and that a water-absorbent agent having high absorbency under no applied pressure and under high pressure can be obtained by controlling, in the post-neutralization process, a neutralization ratio of each of polymer particles prepared from the polymer obtained by post-neutralizing the hydrogel polymer, because this allows a crosslinking process to be efficiently carried out on the surfaces of the polymer particles. Also, the inventors of the present invention have found that in the water-absorbent agent (mass of water-absorbent agent particles) obtained by the described method, the neutralization ratio of the water-absorbent agent particles constituting the water-absorbent agent is highly controlled, and is uniformly neutralized at a particle level, and a change in pH with time of a swollen gel, which is a swollen water-absorbent agent, is small.

After earnest researches to accomplish the above objects, the inventors of the present invention have also found that a water-absorbent agent having high absorbency under no applied pressure and under high pressure wherein the amount of water soluble component is smaller than that of the conventional water-absorbent agent can be stably obtained by subjecting, after post-neutralization, the hydrogel polymer obtained by polymerizing a monomer component including an acid group containing unsaturated monomer (salt) to heat-treatment while maintaining the gel state so as to allow, after drying and pulverizing to a powder, the heat-treated hydrogel polymer to react with a crosslinking agent.

In order to achieve the above-mentioned objects, a water-absorbent agent in accordance with the present invention composed of a plurality of water-absorbent agent particles obtained by post-neutralizing a hydrogel polymer produced by polymerizing a monomer component including an acid group containing unsaturated monomer (salt) is characterized in that:

a neutralization ratio of each of the water-absorbent agent particles is controlled so as to be an allowable neutralization ratio, and absorbency for a saline solution under a load of 50 g/cm$^2$ is not less than 20 g/g.

Also, in order to achieve the above-mentioned objects, a water-absorbent agent in accordance with the present invention composed of a plurality of water-absorbent agent particles is characterized in that a neutralization ratio of each of the water-absorbent agent particles is controlled so as to be an allowable neutralization ratio, and a water soluble component is not more than 20 percent by weight, and absorbency for a saline solution under a load of 50 g/cm$^2$ is not less than 20 g/g.

Also, in order to achieve the above-mentioned objects, a water-absorbent agent in accordance with the present invention composed of a plurality of water-absorbent agent particles is characterized in that a number of water-absorbent agent particles, in 200 particles of the water-absorbent agent particles, having a neutralization ratio lower, by not less than 20 mole percent, than the average neutralization ratio of the water-absorbent agent particles is in a range of not less than 1 and not more than 10.

In order to achieve the above-mentioned objects, a manufacturing method of the water-absorbent agent in accordance with the present invention is characterized by including the step of:

post-neutralizing the hydrogel polymer produced by polymerizing the monomer component including the acid group containing unsaturated monomer (salt), wherein a neutralization ratio of each of polymer particles prepared from a polymer obtained by neutralizing the hydrogel polymer is controlled so as to be an allowable neutralization ratio.

Also, in order to achieve the above-mentioned objects, a manufacturing method of the water-absorbent agent in accordance with the present invention is characterized by including the steps of:

(1) post-neutralizing the hydrogel polymer produced by polymerizing the monomer component including the acid group containing unsaturated monomer (salt);

(2) heat-treating the hydrogel polymer after post-neutralization for a certain period of time while maintaining a gel state;

(3) drying the heat-treated hydrogel polymer to a powder; and (4) allowing the polymer obtained in step (3) to react with a crosslinking agent which is reactive to the functional group of the polymer.

The following describes the present invention in detail.

The hydrogel polymer adopted in the manufacturing method of the water-absorbent agent in accordance with the present invention is a polymer obtained by polymerizing monomer component including an acid group containing unsaturated monomer (salt). As the hydrogel polymer, it is preferable to adopt a hydrogel polymer adopting acrylic acid (salt) as an acid group containing unsaturated monomer (salt), and it is more preferable to adopt a hydrogel polymer obtained by polymerizing acrylic acid (salt) which is 0 mole percent to 40 mole percent neutralized, and it is even more preferable to adopt a free acrylic acid which is 0 mole percent neutralized, namely a hydrogel polymer obtained by polymerizing unneutralized acrylic acid is particularly preferable.

The monomer component includes the acrylic acid (salt) as a main component, and may include other monomers other than the acrylic acid (salt) as required, namely, the monomer component may include other monomers which can be copolymerized with the acrylic acid (salt).

The other monomers which may be included in the monomer component are not particularly limited. Specifically, for example, the following monomers may be included: An acid group containing unsaturated monomer other than acrylic acid, such as methacrylic acid, maleic acid, fumaric acid, crotonic acid, sorbic acid, itaconic acid, cinnamic acid, (anhydrous) maleic acid, β-acryloxy propionic acid, vinyl sulfonic acid, allyl sulfonic acid, vinyl toluene sulfonic acid, styrene sulfonic acid, 2-(meth)acrylamide-2-methylpropanesulfonic acid, 2-(meth)acryloylethanesulfonic acid, 2-(meth)acryloyl propanesulfonic acid, and 2-hydroxyethyl (meth)acryloyl phosphate, and salts thereof; and a nonionic hydrophilic group containing unsaturated monomer such as acrylamide, methacrylamide, N-ethyl(meth)acrylamide, N,N-dimethyl (meth) acrylamide, 2-hydroxyethyl(meth)acrylate, 2-hydroxypropyl(meth) acrylate, methoxypolyethylene glycol (meth)acrylate, polyethyleneglycol mono(meth)acrylate, vinylpyridine, N-vinyl pyrrolidone, N-acryloylpiperidine, and N-acryloyl pyrrolidine. These other monomers may be used individually or in combination by mixing two or more monomers as required. When using the above unsaturated monomers other than acrylic acid, the proportion thereof in the monomer component is set to not more than 50 mole percent, preferably not more than 30 mole percent.

When obtaining the hydrogel polymer, it is preferable to use an inner crosslinking agent so that the crosslinking structure is inside the hydrogel polymer molecule. The inner crosslinking agent is not particularly limited provided that a compound having a plurality of polymerizable unsaturated groups and/or reactive groups in one molecule is adopted. Namely, a compound having a plurality of substituents in one molecule, which can be copolymerized and/or reacted with the acid group containing unsaturated monomer (salt) is adopted. Note that, the hydrogel polymer may have a self-crosslinking structure wherein a crosslinking structure is formed without using the inner crosslinking agent.

The inner crosslinking agent is not particularly limited. Specifically, for example, the following compounds are available: N,N'-methylene-bis(meth)acrylamide, (poly)ethyleneglycol di(meth)acrylate, (poly)propylene glycoldi(meth) acrylate, trimethylolpropane tri(meth)acrylate, trimethylolpropane di(meth) acrylate, glycerol tri(meth)acrylate, glycerol acrylate methacrylate, ethyleneoxidemodified trimethylolpropane tri(meth)acrylate, pentaerythritol tetra(meth)acrylate, dipentaerythritol hexa (meth)acrylate, triallyl cyanurate, triallyl isocyanurate, triallyl phosphate, triallyl amine, poly(meth) allyloxyalkane, (poly)ethyleneglycol diglycidyl ether, glycerol diglycidyl ether, ethylene glycol, polyethyleneglycol, propyleneglycol, glycerol, pentaerythritol, ethylenediamine, polyethyleneimine, and glycidyl (meth)acrylate. These compounds may be used individually or in combination by mixing two or more compounds as required. In the above inner crosslinking agents, by using the one having a plurality of polymerizable unsaturated groups in one molecule, it is possible to further improve the absorbing characteristics, etc., of resulting water-absorbent agent.

Also, as the inner crosslinking agent, an inner crosslinking agent having a plurality of polymerizable unsaturated groups in one molecule is suitably adopted. However, even in such an inner crosslinking agent, (meth)acrylate crosslinking agents having an ester bond, ((poly) ethyleneglycol di (meth) acrylate and trimethylol-propane tri(meth) acrylate, etc.) which is widely adopted for crosslinking polymerization of ordinary absorbent resin, may not produce desirable results in the present invention. Thus, an inner crosslinking agent with no ester bond having a plurality of polymerizable unsaturated groups in one molecule is more suitably adopted in the present invention.

As the inner crosslinking agent with no ester bond, an inner crosslinking agent having a plurality of polymerizable functional groups selected from the group consisting of an allyl group, an amidoester group, and a vinyl group is adopted. For example, as an allyl inner crosslinking agent, the following compounds are available: Acetal such as tetraallyloxyethane; ethers such as polyallyl ether derived from a compound having, in one molecule, two or more hydroxy groups such as pentaerythritol tetraallylether, pentaerythritol triallylether, pentaerythritol diallylether, trimethylolpropane triallylether, trimethylolpropane diallylether, ethyleneglycol diallylether, diethyleneglycol diallylether, triethyleneglycol diallylether, monosaccharide, disaccharide, polysaccharide, and cellulose; and triallyl isocyanurate and triallyl cyanurate. Also, as an amido crosslinking agent, N,N'-methylenebis (meth)acrylamide and N,N'-methylenebis (N-vinylalkylamide), etc., are available. As a vinyl crosslinking agent, divinyl benzene and divinyl ether, etc., are available.

It is preferable that the amount of inner crosslinking agent used with respect to the monomer component, although it depends on types of inner crosslinking agent or target crosslinking density, is in a range of 0.005 mole percent to 3 mole percent, more preferably in a range of 0.01 mole percent to 1.5 mole percent, and even more preferably in a range of 0.05 mole percent to 1 mole percent. When the amount of the inner crosslinking agent used is less than 0.005 mole percent and more than 3 mole percent, a water-absorbent agent having desirable absorbing characteristics may not be obtained.

When forming the crosslinking structure inside the water-absorbent agent using the inner crosslinking agent, the inner crosslinking agent is added to the reactant during or after polymerization of the monomer component, or after polymerization-neutralization.

Note that, in polymerization, it is possible to add to the reactant a hydrophilic polymer such as starch, derivative of starch, cellulose, derivative of cellulose, polyvinyl alcohol, polyacrylic acid (salt), crosslinked polyacrylic acid (salt); or a chain transfer agent such as hydrophosphorous acid (salt), thiol, and thiolic acid.

The method of polymerizing the monomer component is not particularly limited. For example, it is possible to adopt conventionally known methods of aqueous solution polymerization, reversed-phase suspension polymerization, bulk polymerization, and precipitation polymerization, etc. Of these methods, from a view point of easy control of polymerization reaction and the quality of resulting water-absorbent agent, a method in which the monomer component is polymerized in an aqueous solution is preferable, namely, the aqueous solution polymerization and the reversed-phase suspension polymerization are preferable. In the case of adopting the aqueous solution polymerization, it is possible to carry out static polymerization which is performed with virtually no stirring, or stirring polymerization, or a combination of the both. Note that, the aqueous solution polymerization and the reversed-phase suspension polymerization are conventionally known polymerization methods which are disclosed, for example, in U.S. Pat. No. 4,076,663, U.S. Pat. No. 4,625,001, U.S. Pat. No. 4,769,427, U.S. Pat. No. 4,873,299, U.S. Pat. No. 4,093,776, U.S. Pat. No. 4,367,323, U.S. Pat. No. 4,446,261, U.S. Pat. No. 4,683,274, U.S. Pat. No. 4,721,647, and U.S. Pat. No. 5,380,808.

The concentration of the monomer component when adopting the aqueous solution polymerization and the reversed-phase suspension polymerization as a polymerization method, namely, a proportion of the monomer component in the aqueous solution is not particularly limited. However, it is preferable that the concentration be not less than 10 percent by weight and not more than a saturation concentration, more preferably in a range of 15 percent by weight to 40 percent by weight. Also, reaction conditions such as reaction temperature and reaction time are suitably set in accordance with the composition of the monomer component, and therefore it is not particularly limited; nonetheless, polymerization is carried out usually at a temperature in a range of 10° C. to 110° C., more preferably at a temperature in a range of 10° C. to 90° C.

Also, to initiate polymerization, it is possible to adopt a radical polymerization initiator such as potassium persulfate, ammonium persulfate, sodium persulfate, t-buthylhydroperoxide, hydrogen peroxide, and 2,2'-azobis (2-amidinopropane) dihydrochloride; or an active energy radiation such as a UV ray and electron beam. In the case of adopting an oxidative radical polymerization initiator, redox polymerization may be carried out using a reducing agent such as sodium sulfite, sodium hydrogen sulfite, ferrous sulfate, L-ascorbic acid. The amount of the polymerization initiator to be used is preferably in a range of 0.001 mole percent to 2 mole percent, and more preferably in a range of 0.01 mole percent to 0.5 mole percent. Note that, the polymerization initiator is dissolved or diffused in a solvent such as water.

The polymer obtained by the described polymerization, although it depends on the concentration of the aqueous solution of the monomer component, is generally a hydrogel polymer. In the present invention, the hydrogel polymer is further post-neutralized by a neutralizer.

The hydrogel polymer before neutralization may take a form of a gel obtained by the static polymerization, for example, a sheet gel obtained by belt polymerization, a cylindrical gel obtained by cylindrical polymerizer, or a box gel obtained by box polymerizer. Also, the hydrogel polymer may be a particulate gel whose surface area has been increased by chopping a gel (hydrogel polymer) obtained through polymerization or by chopping the gel simultaneously with polymerization or a spherical gel obtained by the reversed-phase suspension polymerization.

In the present invention, post-neutralization is a method in which after polymerizing the monomer component including acrylic acid (salt) which has not been neutralized or has been neutralized to a relatively low neutralization ratio in a predetermined range, resulting polymer is neutralized so as to adjust the neutralization ratio to a desirable value. In the present embodiment, in post-neutralization, after polymerizing monomer components including acrylic acid (salt) having a neutralization ratio of 0 mole percent to 40 mole percent, resulting hydrogel polymer is neutralized so that the neutralization ratio of the polymer produced by neutralizing the hydrogel polymer is adjusted to, preferably, a neutralization ratio of more than 55 mole percent. The neutralization ratio is the mole percent of acrylate in the total weight of the acrylic acid and the acrylate, and considering various properties, environmental friendliness, and safety, the neutralization ratio of the polymer prepared by neutralizing the hydrogel polymer obtained by polymerizing the monomer component including the acrylic acid (salt) is adjusted so that, preferably, the neutralization ratio exceeds 55 mole percent, more preferably in a range of 55 mole percent to 85 mole percent, and even more preferably in a range of 65 mole percent to 75 mole percent. The neutralization ratio of the polymer obtained by neutralizing the hydrogel polymer indicates the neutralization ratio of the neutralized hydrogel polymer (neutralized gel), which is determined by actual measurement or calculation, more precisely, an averaged neutralization ratio of a plurality of polymer particles (mass of polymer particles) which have been obtained by drying and pulverizing the neutralized gel. Also, the desirable neutralization ratio of the polymer obtained by neutralizing the hydrogel polymer is equal to the desirable neutralization ratio of resulting water-absorbent agent.

Note that, as a conventional manufacturing method of the water-absorbent agent, a method in which a water-absorbent agent is obtained by polymerizing acrylic acid which has been neutralized beforehand so as to have a desired neutralization ratio is available (Japanese Unexamined Patent Application No. 126310/1989 (Tokukaihei 1-126310), and U.S. Pat. No. 4,985,518). However, the water-absorbent agent obtained by this method contains a relatively large amount of water soluble component, and in the case where such a water-absorbent agent is adopted for sanitary articles, there is a chance that the diffusivity of aqueous liquid such as body fluid is lowered and the backlash of the aqueous liquid is increased. Thus, this method is not suitable.

The water-absorbent agent of the present invention can be stably obtained with ease by controlling the neutralization ratio of each of the polymer particles prepared from the polymer produced by post-neutralizing the hydrogel polymer which is produced by polymerizing the monomer component including the acid group containing unsaturated monomer. Specifically, after post-neutralizing the hydrogel polymer obtained by polymerizing the monomer component including the acid containing unsaturated monomer (salt) so that the neutralization ratio thereof is not more than a predetermined value, resulting polymer is allowed to react with a crosslinking agent which is reactive to the functional group of the polymer, thus stably obtaining the water-absorbent agent of the present invention with ease.

In the present invention, a neutralization coefficient is a new parameter which indicates the neutralization state of the polymer obtained by neutralizing the hydrogel polymer formed by polymerizing the acid group containing unsaturated monomer, the neutralization state being indicated by a number of particles, in a predetermined number of polymer particles prepared by drying and pulverizing the polymer, having a non-allowable neutralization ratio. In the present embodiment, a first neutralization coefficient indicates the neutralization state when (a) a polymer obtained through post-neutralization by polymerizing a monomer component including an acid group containing monomer, preferably acrylic acid (salt) and (b) a crosslinking agent reactive to the functional group of the polymer are mixed and reacted, wherein the first neutralization coefficient is indicated by a number of polymer particles, in a predetermined number of polymer particles prepared by drying and pulverizing the polymer, having a neutralization ratio lower than the first allowable neutralization ratio. Also, a second neutralization coefficient indicates the neutralization state of the above polymer, wherein the second neutralization coefficient is indicated by a sum of (A) the number of polymer particles, in a predetermined number of the polymer particles, having a neutralization ratio lower than a second allowable neutralization ratio and (B) the number of polymer particles having a neutralization ratio higher than the second allowable neutralization ratio.

The following describes the measuring method of the neutralization coefficient of the present invention referring to FIG. 2.

First, as shown in FIG. 2, on the lower surface side of a plastic plate 22 having a thickness of 1.6 mm provided with an opening section 22a with a size of 20 mm×20 mm, a cover glass 23' having a size of 25 mm×25 mm is attached by a transparent adhesive tape (not shown) so as to cover the opening section 22a. Then, in a vicinity of the center of the opening section 22, 200 particles of polymer particles 21 which have been classified into 300 μm to 600 μm are dispersed. Thereafter, 0.2 ml of deionized water is added to the polymer particles 21 with a micro syringe. Then, just before all the deionized water is absorbed by the polymer particles 21 by swelling, 0.05 ml of mixed solution of 0.1 percent of ethanol solution of bromothimol blue (BTB) and 0.1 percent of ethanol solution of methyl red (MR) in a ratio of 1.5 to 1 is added with a micro syringe. As a result, a colored swollen gel is produced. Thereafter, on the upper surface side of the plastic plate 22, a cover glass 23 having a size of 25 mm×25 mm is placed so as to cover the opening section 22a, and the swollen gel in the opening section 22a covered by the cover glass 23 and 23' is spread. Then, in the colored gel particles constituting the swollen gel, a number of particles having a color corresponding to that of comparative particles is measured, and the number represents the neutralization coefficient.

Note that, since the cover glass 23 and 23' are transparent and the transparency of the gel particles is sufficient, and the gel particles are approximately aligned in a single layer in the opening section 22a, even when the gel particles partially overlap, all the gel particles can be observed through the upper and lower surfaces of the plastic plate 22.

Here, in the case where the first neutralization coefficient is adopted as a neutralization coefficient, the comparative particles are particles which have been classified into 300 μm to 600 μm, obtained by drying each hydrogel polymer having a neutralization ratio of lower, by not less than 20 mole percent, than a desirable neutralization ratio (neutralization ratio of a polymer obtained by neutralizing the hydrogel polymer which is formed by polymerizing monomer component including acid containing monomer, preferably acrylic acid, more precisely, an averaged neutralization ratio of a mass of polymer particles prepared by drying and pulverizing the neutralized polymer). The comparative particles also include particles obtained by drying hydrogel polymer before neutralization (hydrogel polymer with a neutralization ratio of 0 mole percent). Here, when a reference is made to particles having a color corresponding to the color of the comparative particles, it is meant that the particles have a color corresponding to the color of the comparative particles resulting from addition of the mixed indicator. Namely, in the case of neutralizing the hydrogel polymer having a neutralization ratio of 0 mole percent to a neutralization ratio of 75 mole percent, the color of the comparative particles is the color of particles, resulting from addition of the mixed indicator, which are obtained by drying, without post-neutralization, the hydrogel polymer formed by polymerizing acrylic acid (salt) with a neutralization ratio of 0 mole percent to 55 mole percent.

In the present invention, it is preferable that the number of particles having a color corresponding to that of the comparative particles is determined by measuring the number of particles having a color corresponding to the color of particles, resulting from addition of the mixed indicator, which have been classified into 300 $\mu$m to 600 $\mu$m, obtained by drying the hydrogel particles having a neutralization ratio which is lower, by not less than 20 mole percent, than a desirable neutralization ratio.

However, considering the various properties, environmental friendliness, and safety, it is preferable to adjust the neutralization ratio of the polymer obtained by neutralizing the hydrogel polymer adopted as the material of the water-absorbent agent, namely, the average neutralization ratio of the plurality of polymer particles (mass of polymer particles) obtained by drying and pulverizing the polymer is adjusted to a neutralization ratio of more than 55 mole percent, more preferably in a range of 65 mole percent to 75 mole percent. Also, because a water-absorbent agent having superior absorbency under high pressure can be obtained by controlling the neutralization ratio of the polymer particles to exceed 55 mole percent, it is possible, in the measurement of the number of particles having a color corresponding to the color of the comparative particles, that the color of particles corresponding to the color of the comparative particles is the color, resulting from addition of the mixed indicator, of the comparative particles which are obtained by drying in particular, in a hydrogel polymer with a neutralization ratio of lower, by not less than 20 percent, than the desirable neutralization ratio, a hydrogel polymer with a neutralization ratio of not more than 55 mole percent. Also, as the comparative particles, it is possible to adopt, instead of the hydrogel polymer having a neutralization ratio in the above-mentioned range, particles of a crosslinked polyacrylic acid having a neutralization ratio in the above-mentioned range.

In the present invention, the number of polymer particles, in the mass of the polymer particles, having a non-allowable neutralization ratio is determined by measuring the number of polymer particles, in the mass of the polymer particles, having a color corresponding to the color of the comparative particles.

Also, after earnest research, the inventors of the present invention have found that in the case of carrying out a surface crosslinkage on a polymer which is obtained by neutralizing the hydrogel polymer, the presence of a highly neutralized polymer with a neutralization ratio of not less than 95 mole percent prevents the effect of the surface crosslinkage. Especially, when a free alkali is remaining in the polymer, even when the residual amount is minute, the absorbency under high pressure is greatly reduced by more than the amount which would be expected from such a minute amount of residual alkali.

Further, the inventors of the present invention also found that in the polymer particles having a neutralization ratio of not more than 55 mole percent, the presence of polymer particles having a neutralization ratio of not more than 30 mole percent in particular greatly reduces the mixing ability and the degree of dissociation of the surface crosslinking agent and prevents the absorbency under high pressure from increasing by more than the amount which would be expected from the presence of the polymer particles with such a neutralization ratio.

Therefore, in the present invention, the second allowable neutralization ratio is the neutralization ratio of the polymer particles in a range of more than 30 mole percent and less than 95 mole percent, and the neutralization ratio indicated by the sum of (a) the number of polymer particles with a neutralization ratio of not more than 30 mole percent and (b) the number of polymer particles with a neutralization ratio of not less than 95 mole percent is the second neutralization coefficient. Also, in the present invention, the neutralization ratio of each of the polymer particles is controlled so that the neutralization ratio thereof is in a range of more than 30 mole percent and less than 95 percent, and the hydrogel polymer is neutralized so that the second neutralization coefficient is not more than a predetermined value, thus stably obtaining a water-absorbent agent having superior absorbency under high pressure.

Here, in the case where the second neutralization coefficient is adopted as a neutralization coefficient, the comparative particles are particles which have been classified into 300 $\mu$m to 600 $\mu$m, obtained by drying each hydrogel polymer having a neutralization ratio of not more than 30 mole percent, and are particles which have been classified into 300 $\mu$m to 600 $\mu$m, obtained by drying each hydrogel polymer having a neutralization ratio of not less than 95 mole percent. When adopting the second neutralization coefficient, it is also possible to adopt, as the comparative particles, the particles of the polyacrylic acid crosslinking agent having a neutralization ratio in the above-mentioned range.

Note that, in the measurement of the neutralization coefficient, when the mixed indicator is added to the polymer particles 21, the color continuously changes from red, orange, yellow, green yellow, to green as the neutralization ratio of the polymer particles is increased.

Thus, in order to conveniently measure the first neutralization coefficient, when measuring the number of particles having a color corresponding to the color of the comparative particles, the number of particles having a color the same as, and the number of particles having a color which is more red than the color, resulting from addition of the mixed indicator, of particles obtained by drying the hydrogel polymer (or polyacrylic acid crosslinking agent with a neutralization of 55 mole percent) having a neutralization ratio of lower, by 20 mole percent, than the desirable neutralization ratio are measured.

Similarly, in order to conveniently measure the second neutralization coefficient, when measuring the number of particles having a color corresponding to the color of the comparative particles, the number of particles having a color the same as, and the number of particles having a color which is more red than the color, resulting from addition of the mixed indicator, of particles obtained by drying the hydrogel polymer (or polyacrylic acid crosslinking agent with a neutralization of 30 mole percent) having a neutralization ratio of 30 mole percent, and the number of particles having a color the same as, and the number of particles having a color which is more green than the color, resulting from addition of the mixed indicator, of particles obtained by drying the hydrogel polymer (or polyacrylic acid crosslinking agent with a neutralization of 95 mole percent) having a neutralization ratio of 95 mole percent are measured.

Note that, in the case where the comparative particles having a size of 300 μm to 600 μm are not present, the measurement may be carried out with respect to particles having a size of 150 μm to 300 μm, or 600 μm to 850 μm.

As described, in the present invention, when the allowable neutralization ratio of the polymer particles is $Z_1$ (mole percent), and the average neutralization ratio of the polymer particles is $Z_2$ (mole percent), the first allowable neutralization ratio is a neutralization ratio which satisfies the relation:

$$Z_1 > Z_2 - 20 \text{(mole percent)}$$

Namely, a neutralization ratio which is not lower, by not less than 20 mole percent, than the average neutralization ratio of the polymer particles, or a neutralization ratio which exceeds 55 mole percent. Also, a non-first allowable neutralization ratio is a neutralization ratio which is lower, by not less than 20 mole percent, than the average neutralization ratio of the polymer particles, or a neutralization ratio of not more than 55 mole percent.

Also, in the present invention, the second allowable neutralization ratio is a neutralization ratio in a range of more than 30 mole percent and less than 95 mole percent, and the non-second allowable neutralization ratio is a neutralization ratio of not more than 30 mole percent, or a neutralization ratio of not less than 95 mole percent.

Specifically, as a post-neutralization method, the following methods ① and ② are available. ① A method in which the post-neutralization is carried out so that the first neutralization coefficient is not more than 10, and ② a method in which the post-neutralization is carried out so that the second neutralization coefficient is not more than 30. Of the two methods ① and ②, the method ① is more preferable. Also, for the described reason, it is particularly preferable that the post-neutralization is carried out so as to satisfy the conditions for neutralization coefficients of the method ① and the method ②, respectively.

In the present invention, in the case of adopting the method ①, a water-absorbent agent having superior absorbency under high pressure can be stably obtained when the number of polymer particles having the non-first allowable neutralization ratio in 200 particles of the polymer particles is not more than 10 (Namely, when a proportion of the number of polymer particles having the first allowable neutralization ratio in the mass of the polymer particles is more than 95 percent, and when a proportion of the number of polymer particles having the non-first allowable neutralization ratio is not more than 5 percent). However, as mentioned above, the presence of highly neutralized polymer, having a neutralization ratio of not less than 95 mole percent prevents the effect of surface crosslinkage. Therefore, a water-absorbent agent having superior absorbing characteristics and high absorbency especially under high pressure can be stably obtained when the sum of (a) the number of polymer particles having the first allowable neutralization ratio and (b) the number of polymerized polymer having a neutralization ratio of not less than 95 mole percent is not more than 10 in 200 particles of the polymerized polymer (Namely, when a proportion of the number of polymer particles having a neutralization ratio in a range of more than 55 mole percent and less than 95 percent in the mass of the polymer particles is larger than 95 percent, and when a proportion of the sum of (a) the number of polymer particles having a neutralization ratio of not more than 55 mole percent and (b) the number of polymer particles having a neutralization of not less than 95 mole percent is not more than 5 percent, or when a proportion of the number of polymer particles having a neutralization ratio of not lower, by not less than 20 mole percent, than the average neutralization ratio of the polymer particles in the mass of the polymer particles and a proportion of the number of polymer particles having a neutralization ratio of less than 95 mole percent is larger than 95 percent, and when a proportion of the sum of (A) the number of polymer particles having a neutralization ratio of lower, by not less than 20 mole percent, than the average neutralization ratio of the polymer particles and (B) the number of polymer particles having a neutralization of not less than 95 mole percent is not more than 5 percent).

Also, in the present invention, even when the first neutralization coefficient exceeds 10, provided that the second neutralization coefficient is not more than 30, compared with the conventional example, it is possible to stably obtain a water-absorbent agent having superior absorbing characteristics and superior absorbency especially under high pressure.

In the present invention, it is required that the first neutralization coefficient be not more than 10 (namely, not less than 0 and not more than 10), preferably not more than 5. Also, it is required that the second neutralization coefficient be not more than 30 (namely, not less than 0 and not more than 30), preferably not more than 20. Note that, the neutralization coefficient of 0 indicates, in the measuring method of neutralization coefficient, that the particle having a color corresponding to the color of the comparative particles is not present, namely, the neutralization has completed so that a desirable neutralization ratio has been obtained uniformly at the polymer particle level.

In the manufacturing method ①, (a) the polymer produced by polymerizing the monomer component including the acrylic acid (salt) and (b) the crosslinking agent which is reactive to the functional group of the polymer should be reacted with each other preferably after the hydrogel polymer is adjusted to have particle size distribution close to the particle size distribution of the water-absorbent agent as the final product by drying and pulverizing after post-neutralization. Thus, the hydrogel polymer is neutralized in such a manner that the first neutralization coefficient of the polymer particles as a precursor of the water-absorbent agent, which have been adjusted to have particle size distribution close to the particle size distribution of the water-absorbent agent as the final product by drying and pulverizing, is not more than 10 and/or the second neutralization coefficient thereof is not more than 30.

Also, because the neutralization state of the hydrogel polymer is maintained even after the crosslinking reaction, the neutralization coefficient of the polymer particles in the crosslinking reaction is maintained also in the water-absorbent agent as the final product unless the water-absorbent agent takes the form of the swollen gel by absorption of water. That is to say, the neutralization coefficient of the polymer particles is the neutralization coefficient of the water-absorbent agent. Note that, the neutralization coefficient of the water-absorbent agent as the final product can also be measured by the same method as the method for measuring the neutralization coefficient of the polymer particles which are prepared by polymerizing the monomer component including the acrylic acid (salt).

Also, because the desirable neutralization ratio of the water-absorbent agent is equal to the desirable neutralization ratio of the polymer which is obtained by neutralizing the hydrogel polymer, and the neutralization coefficient of the polymer particles prepared from the polymer is maintained even after manufacturing of the water-absorbent agent, in the present invention, the allowable neutralization ratio of the water-absorbent agent particles constituting the water-absorbent agent is equal to the allowable neutralization ratio of the polymer particles. Thus, when the allowable neutralization ratio of the water-absorbent agent particles is $Z_1$ (mole percent), and the average neutralization ratio of the mass of the water-absorbent agent particles is $Z_2$ (mole percent), the first allowable neutralization ratio of the water-absorbent agent particles is the neutralization ratio which satisfies the relation:

$$Z_1 > Z_2 - 20 \text{(mole percent)}$$

Namely, a neutralization ratio which is not lower, by not less than 20 mole percent, than the average neutralization ratio of the polymer particles, or a neutralization ratio which exceeds 55 mole percent. Also, the non-first allowable neutralization ratio of the water-absorbent agent particles is the neutralization ratio which is lower, by not less than 20 percent, than the average neutralization ratio of the water-absorbent agent particles, or the neutralization ratio of not more than 55 mole percent. Also, in the present invention, the second allowable neutralization ratio of the water-absorbent agent particles is the neutralization ratio in a range of more than 30 mole percent and less than 95 mole percent, and the non-second allowable neutralization ratio is the neutralization ratio of not more than 30 mole percent, or a neutralization ratio of not less than 95 mole percent.

As described, the neutralization coefficient is represented by the number of particles having a color corresponding to the color of the comparative particles in the polymer particles 21, namely, the number of particles which do not fall in the range of the allowable neutralization ratio (particles having non-allowable neutralization ratio, hereinafter referred to as non-neutralized particles) represents the neutralization coefficient, thus making it possible to examine how uniformly the polymer particles are neutralized at the particle level. Also, since a lower neutralization coefficient means less change in pH in polymer particles and more safety, it is possible to achieve the object of the present invention to stably obtain a water-absorbent agent having superior absorbency under high pressure and high load. In short, the neutralization coefficient is especially important in stably obtaining a water-absorbent agent having high absorbency under high pressure and high load, containing less amount of water-soluble component than the conventional water-absorbent agent with an improved safety, and having less change in pH of the swollen gel.

For example, the afore-mentioned applications disclose water-absorbent resin which is produced by neutralizing a hydrogel polymer formed by polymerizing the monomer component including acrylic acid (salt), and by crosslinking the neutralized polymer. However, these U.S. Patents do not take into consideration of uniformity of neutralization state of the polymer at the particle level when a crosslinking agent is allowed to react with a post-neutralized polymer which has been dried and pulverized to adjust the particle size close to that of the water-absorbent agent as the final product, and even when the neutralization on the surface of the polymer is uniform, usually, the neutralization state of the polymer particles is not uniform at the particle level when the surface crosslinkage is carried out after the polymer is dried and pulverized.

Namely, conventionally, the end point of neutralization of the hydrogel polymer is when the basic substance in the hydrogel polymer is not observed neither by a naked eye nor an indicator, specifically, when coloration (red) induced by phenolphthalein is not observed even when the phenolphthalein is added to the hydrogel polymer. However, in this hydrogel polymer, namely, the polymer obtained through post-neutralization process, which is used as a material of the conventional water-absorbent agent, might have a desirable neutralization ratio at the macro level, but such a desirable neutralization ratio is not exhibited by each polymer particle when the polymer particles are examined at the micro level.

In actual practice, when the uniformity of the neutralization state of the polymer obtained through the conventional post-neutralization process is examined in accordance with the first neutralization coefficient of the present invention, conventional polymer particles have higher first neutralization coefficient compared with that of the present invention, and as shown in FIG. 4, a large number of non-neutralized particles 21b are observed with the particles (referred to as neutralized particles hereinafter) 21a which fall in a range of the allowable neutralization ratio.

In the water-absorbent resin (water-absorbent agent) obtained by allowing a polymer having such a large neutralization coefficient to react with a crosslinking agent which is reactive to the functional group of the polymer, absorbency under low pressure can be increased to a certain level; however, it is difficult to increase the absorbency to a certain level under high pressure. Further, the pH of swollen gel, which is a swollen water-absorbent resin, changes with time. Therefore, in order to achieve the object of the present invention, that is to improve the absorbency under high pressure, it is critical that the first neutralization coefficient be not more than 10 and/or the second neutralization coefficient be not more than 30. When the neutralization ratio exceeds the above limits, the absorbency under no load (no applied pressure) and under low pressure does not change significantly; however, absorbency of the entire water-absorbent particles under high pressure is reduced significantly for more than an amount which is expected from the proportion of particles having a color corresponding to the color of the comparative particles (for example, 10/200 particles or 30/200 particles).

As a method for neutralizing the hydrogel polymer, for example, Japanese Publication for Unexamined Patent Application No. 131209/1989 (Tokukaihei 1-131209) discloses a method in which a neutralizer or an aqueous solution of the neutralizer is added and mixed with the hydrogel polymer while chopping the hydrogel polymer into small particles in a container having a plurality of rotation shafts by the shear force exerted by the rotation of the rotation shafts. However, such a method is not sufficient in realizing the neutralization coefficient of the present invention.

Specifically, in order to achieve the neutralization coefficient of the present invention, the following methods are available:

(1) A method for inducing rearrangement of neutralizer by adding the neutralizer to the hydrogel polymer with enough stirring, and thereafter by adding an aqueous liquid.

(2) A method for filtering the hydrogel polymer after sufficiently soaking the hydrogel polymer in a neutralizer solution containing a neutralizer in an amount larger than the amount of neutralizer required for achieving a desired degree of neutralization.

(3) A method for mixing a neutralizer with the hydrogel polymer for an extended period of time while stirring, the neutralizer being mixed in the form of a fine droplet having a size in a range of 1 µm to 1000 µm.

(4) A method for adding a neutralizer after adjusting the particle diameter of the hydrogel polymer in a range of 1 µm to 1000 µm.

(5) A method for leaving a hydrogel polymer to which a neutralizer has been added under high pressure or under applied pressure.

(6) A method for irradiating a hydrogel polymer to which a neutralizer has been added with a micro wave, a ultrasonic wave, or other electromagnetic waves.

(7) A method for leaving a hydrogel polymer to which a neutralizer has been added for not less than 24 hours (until the neutralization coefficient of the present invention is reached).

(8) A method for adding and mixing a neutralizer with the hydrogel polymer in the presence of a surface active agent or an inorganic powder.

(9) A method for directly spreading an aqueous solution of a neutralizer without using an organic solvent onto the particulate hydrogel polymer which has been obtained by the reversed-phase suspension polymerization.

(10) A method for mixing an aqueous solution of a neutralizer with a powder (precursor of water-absorbent agent) whose particle is close to that of the water-absorbent agent (final product) which is obtained by drying, and as required, by pulverizing the hydrogel polymer.

(11) A method for filtering a powder (precursor of water-absorbent agent) after sufficiently soaking in a neutralizer solution containing a neutralizer in an amount larger than the amount of neutralizer required for achieving a desired degree of neutralization.

(12) A method for allowing the hydrogel polymer to react with a gaseous neutralizer such as ammonia.

Of the above (1) through (12) methods, the method (1) is particularly preferable because of the short period of time required for achieving with ease the neutralization coefficient of the present invention and a water-absorbent agent having superior absorbency.

The neutralizer for achieving the neutralization coefficient of the present invention is not particularly limited so that it is possible to adopt conventionally known inorganic acids or bases or organic acids or bases. As the neutralizer, for example, specifically the following compounds are available: sodium hydroxide, potassium hydroxide, lithium hydroxide, ammonium hydroxide, sodium carbonate, potassium carbonate, ammonium carbonate, sodium bicarbonate, potassium bicarbonate, ammonium bicarbonate, sodium phosphate, potassium phosphate, ammonium phosphate, sodium borate, potassium borate, ammonium borate, sodium acetate, potassium acetate, ammonium acetate, sodium lactate, potassium lactate, ammonium lactate, sodium propionate, potassium propionate, and ammonium propionate.

These neutralizer may be used individually or in combination by mixing two or more compounds as required. In the above neutralizers, in the case of post-neutralizing the hydrogel polymer obtained by polymerizing the monomer component whose main component is the acrylic acid, it is preferable to adopt hydroxides of monovalent positive ions such as sodium hydroxide, potassium hydroxide, lithium hydroxide, and ammonium hydroxide; or carbonates of monovalent positive ions such as sodium carbonate, potassium carbonate, ammonium carbonate, sodium bicarbonate, potassium bicarbonate, and ammonium bicarbonate, since these compounds are industrially easy to obtain, and have desirable properties, and efficiently lower the neutralization coefficient.

Also, in the case of adopting the method for neutralizing the hydrogel polymer having a high pH using inorganic acid or organic acid, namely, even when a method in which a hydrogel polymer is neutralized with an acid after the polymer is once made alkaline is used, as long as the neutralization coefficient is in the range of the present invention, it is possible to stably obtain a water-absorbent agent having superior absorbency under high pressure and high load. As the inorganic acid or organic acid to be adopted in this method, for example, phosphoric acid, sulfuric acid, hydrochloric acid, carbonic acid, nitric acid, citric acid, and lactic acid, etc., are available; however, the compounds are not limited to these, and they may be used individually or in combination by mixing two or more compounds as required.

Although the neutralizer such as above can be added to the hydrogel polymer in the form of an aqueous solution, slurry, or a fine particle such as a powder and a granule, it is preferable to use the neutralizer in the form of an aqueous solution since this reduces the time required for reaching the neutralization coefficient.

As the aqueous liquid adopted in method (1), water is preferable; however, an aqueous liquid including water as a main component may also include salts other than a base, or a hydrophilic organic solvent, etc., in a proportion which does not interfere with the objects of the present invention.

When adding the aqueous liquid during neutralization of the hydrogel polymer, it is preferable that the aqueous liquid be added after it is confirmed that the surface of the hydrogel polymer has been neutralized to a pH in a target pH range. In order to confirm neutralization, a neutralization indicator such as phenolphthalein is suitable.

It is preferable that the amount of aqueous liquid to be added is, with respect to 100 parts by weight of hydrogel polymer, in a range of 2 parts by weight to 100 parts by weight, more preferably in a range of 5 parts by weight to 100 parts by weight, or even more preferably in a range of 10 parts by weight to 50 parts by weight. When the amount of aqueous liquid to be added in less than 2 parts by weight, the time required for reducing the neutralization coefficient below a predetermined value becomes too long. On the other hand, when the amount of aqueous liquid to be added exceeds 100 parts by weight, it becomes difficult to dry the hydrogel polymer, and too much weight is put on the drying process for finishing the product, thus industrially not preferable.

When adding the aqueous liquid, it is preferable that the aqueous liquid and the hydrogel polymer be mixed and kneaded continuously or discontinuously. Also, in order to complete neutralization, it is preferable to maintain the mixture for not less than 1 hour, more preferably not less than 2 hours, even more preferably not less than 6 hours, or most preferably not less than 12 hours. It is preferable that the maintaining temperature of the neutralized gel after heat-treatment be in a range of 0° C. to 80° C., and more preferably in a range of 5° C. to 50° C. without a change in the water content of the hydrogel polymer. Also, it is more preferable that the amount of aqueous liquid and the maintaining time are selected so that the first neutralization coefficient is not more than 5 and/or the second neutralization coefficient is not more than 20.

As described, the polymer which is post-neutralized by the manufacturing method in accordance with the present invention has a first neutralization coefficient of not more than 10 and/or a second neutralization coefficient of not more than 30, and as shown in FIG. 1, the unneutralized particles 21b are fewer compared with the conventional example, and are neutralized more uniformly at the particle level.

The water-absorbent agent in accordance with the present invention is obtained by allowing the polymer which has been post-neutralized to react with a crosslinking agent which is reactive to the functional group of the polymer so as to carry out surface crosslinkage. In this manner, by processing the polymer whose neutralization ratio has been controlled at particle level in the presence of a crosslinking agent (referred to as surface crosslinking agent hereinafter) so as to carry out surface crosslinkage, it is possible to increase the crosslinking density in a vicinity of the polymer surface compared with the crosslinking density inside the polymer, thus obtaining a water-absorbent agent having superior absorbency.

Although the polymer may be reacted with the crosslinking agent without adjusting the water content, in order to increase, to the maximum, the absorbency of the final product under high pressure, it is preferable that the crosslinking agent be added and reacted to the polymer after (1) adjusting the water content preferably to not more than 10 percent by weight, (2) pulverizing as required, and (3) adjusting the particles to a desirable particle size.

The drying method of the polymer is not particularly limited so that a variety of conventionally known drying methods such as hot-air drying, thin-film drying using a drum dryer, reduced-pressure drying, fluid bed drying, and freeze drying may be adopted. The drying temperature of the polymer is not particularly limited, but a temperature in a range of 80° C. to 230° C. is adopted. Also, the pulverizing method is not particularly limited so that a variety of conventionally known pulverizing methods such as a method using a hammer granulator, a roll granulator, or a jet-air granulator may be adopted.

The polymer obtained as a precursor of the water-absorbent agent in the described manner is a discrete particle or an aggregate which takes a wide variety of shapes such as an irregular crushed shape, a spherical shape, an irregular granular shape, a rod shape, a substantially spherical shape, and a flat shape, and it is preferable that the water content of the polymer is not more than 10 percent by weight, more preferably not more than 5 percent by weight. Also, the average diameter of the polymer particles obtained by pulverizing and classifying the dried polymer is in a range of 200 μm to 600 μm, and more preferably the proportion of particles having a diameter of not more than 150 μm is not more than 10 percent by weight, even more preferably, not more than 5 percent by weight.

The surface crosslinking agent to be adopted here is not particularly limited provided that a compound which is reactive to the functional group of the polymer is adopted. Specifically, for example, the following compounds can be adopted as the surface crosslinking agent: a polyhydric alcohol compound such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,4-butanediol, 1,5-pentanediol, 1,6-hexanediol, 1,2-cyclohexanedimethanol, 1,2-cyclohexanol, trimethylol propane, diethanolamine, triethanolamine, polyoxypropylene, oxyethylene-oxypropylene block copolymer, pentaerythritol, and sorbitol; and a polyepoxy compound such as ethyleneglycol diglycidyl ether, polyethyleneglycol diglycidyl ether, glycerol polyglycidyl ether, diglycerol polyglycidyl ether, polyglycerol polyglycidyl ether, polypropylene glycol diglycidyl ether, and glycidol; and polyamine compounds such as ethylenediamine, diethylenetryamine, triethylenetetraamine, tetraethylenepentaamine, pentaethylenehexaamine, polyallyl amine, and polyetylene imine; and a polyisocyanate compound such as 2,4-tolylene diisocyanate and hexamethylene diisocyanate; and a polyoxazoline compound such as 1,2-ethylene bisoxazoline; and an alkylene carbonate compound such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydromethyl-1,3-dioxolane-2-one, 1,3-dioxane-2-one, 4-methyl-1,3-dioxane-2-one, 4,6-dimethyl-1,3-dioxane-2-one, and 1,3-dioxopane-2-one; and a haloepoxy compound such as epichlorohydrin, epibromohydrin, and α-methyl epichlorohydrin; and a silane coupling agent such as γ-aminopropyltrimetoxy silane; and a polyvalent metal such as a hydroxide or a chloride of zinc, calcium, magnesium, alminium, iron, and zirconium.

These surface crosslinking agents may be used individually or in combination by mixing two or more compounds as required. In the above surface crosslinking agents, it is preferable to use a surface crosslinking agent having a composition of a first surface crosslinking agent and a second surface crosslinking agent whose solubility parameters (SP values) are different (see U.S. Pat. No. 5,422,405), because this results in a water-absorbent agent having superior absorbency especially under high pressure. Note that, the solubility parameter has a value which is generally adopted as a factor which represents the polarity of the compound. In the present invention, the value of solubility parameter δ $(cal/cm^3)^{1/2}$ specified on pages 527 to 539 of The Polymer Handbook, 3rd Edition (published by Wiley Interscience Publication) is adopted. Also, as the solubility parameter of a solvent, which is not specified on the above pages, a value which is obtained by substituting the Hoy cohesive energy constant into the Small equation specified on page 524 of The Polymer Handbook is adopted.

As the first surface crosslinking agent, it is preferable to adopt a compound which is reactive to the functional group of the polymer, whose solubility parameter is not less than $12.5(cal/cm^3)^{1/2}$, more preferably not less than $13.0 (cal/cm^3)^{1/2}$. Specifically, as the first surface crosslinking agent, for example, the following compounds are available: ethylene glycol, propylene glycol, glycerol, pentaerythritol, sorbitol, ethylene carbonate (1,3-dioxolane-2-one), propylene carbonate (4-methyl-1,3-dioxolane-2-one), and other compounds. However, the first crosslinking agent is not limited to the above compounds. These compounds may be used individually or in combination by mixing two or more compounds as required.

As the second surface crosslinking agent, it is preferable to adopt a compound which is reactive to the functional group of the polymer, whose solubility parameter is less than $12.5(cal/cm^3)^{1/2}$, more preferably in a range of $9.5(cal/cm^3)^{1/2}$ to $12.0(cal/cm^3)^{1/2}$. Specifically, as the second surface crosslinking agent, for example, the following compounds are available: diethylene glycol, triethylene glycol, tetraethylene glycol, 1,3-propanediol, 1,4-butabediol, 1,5-pentanediol, 1,6-hexanediol, 2,5-hexanediol, trimethylol propane, ethylene glycol diglycidyl ether, polyethylene glycol diglycidyl ether, glycerol polyglycidyl ether, polyglycerol polyglycidyl ether, propylene glycol diglycidyl ether, polypropylene glycol diglycidyl ether, and other compounds. However, the second crosslinking agent is not limited to the above compounds. These compounds may be used individually or in combination by mixing two or more compounds as required.

It is preferable that the amount of surface crosslinking agent used, namely, the total amount of the first surface crosslinking agent and the second surface crosslinking agent is, although it depends on types of the crosslinking agents adopted and how they are combined, with respect to 100 parts by weight of the solid component of the final water-absorbent agent, in a range of 0.001 part by weight to 10 parts by weight, more preferably in a range of 0.01 part by weight to 5 parts by weight. When the amount of surface crosslinking agent used is in the above range, it is possible to make the crosslinking density higher in a vicinity of the surface of the water-absorbent agent than the inside thereof, thus obtaining a water-absorbent agent having superior absorbency under applied pressure regardless of the amount of load. The amount of crosslinking agent of less than 0.001 part by weight is not preferable because of the possibility that the improvement on the absorbency under applied pressure is not sufficiently obtained. Also, the amount of the crosslinking agent of more than 10 parts by weight is not preferable because it is non-economical as the added crosslinking agent is not efficiently used, and the surface crosslinking agent is used in excess when a crosslinking structure most suitable to the water-absorbent agent is formed, raising the possibility that the absorbency is lowered excessively.

When mixing the polymer with the crosslinking agent, it is possible to add, as required, water, water vapor, or an aqueous liquid containing water and hydrophilic organic solvent during or after mixing. Here, in the case where the surface crosslinking agent is a compound which reacts with the polymer by covalent bonding, such as a polyhydric alcohol compound, a polyepoxy compound, and alkylene carbonate, it is preferable to add, as a solvent, water, water vapor, or an aqueous liquid containing water and hydrophilic organic solvent, because this might increase significantly the absorbency under applied pressure.

Specifically, as the hydrophilic organic solvent, although not limited, for example, the following compounds are available: lower alcohols such as methyl alcohol, ethyl alcohol, n-propyl alcohol, isopropyl alcohol, n-butyl alcohol, isobutyl alcohol, and t-butyl alcohol; and ketones such as acetone; and ethers such as dioxane, alcoxy(poly) ethylene glycol, and tetrahydrofuran; and amides such as N,N-dimethylformamide; and sulfoxides such as dimethylsulfoxide.

Here, the amount of water used, although it depends on types or the particle diameter of the polymer, with respect to 100 parts by weight of the solid component of the polymer, is not more than 10 parts by weight, more preferably in a range of 1 part by weight to 5 parts by weight. Also, the amount of hydrophilic organic solvent used, although it depends on types or the particle diameter of the polymer, with respect to 100 parts by weight of the solid component of the polymer, is not more than 10 parts by weight, more preferably in a range of 0.1 part by weight to 5 parts by weight.

When the polymer is mixed with the surface crosslinking agent, for example, it is possible to (1) add the surface crosslinking agent after dispersing the polymer in the aqueous liquid or (2) directly spray or drop the surface crosslinking agent which has been dissolved in water or in aqueous liquid onto the polymer. Also, in the case where water is used in mixing, it is possible that the water is a mixture of powder in the form of water-insoluble fine particles, a surface active agent, and a variety of organic or inorganic acids, etc.

It is preferable that, in order to ensure that the polymer and the surface crosslinking agent are mixed together uniformly, the mixer for mixing the polymer and the surface crosslinking agent has a large mixing force. As the mixer, for example, the following devices are suitably adopted: a cylindrical mixer, a double-walled conical mixer, a V-shaped mixer, a ribbon type mixer, a screw mixer, floating rotary disk mixer, an airborne mixer, a twin arm type kneader, inner mixer, pulverizing kneader, a roll mixer, and a screw plodder.

For an unknown reason, the polymer having a specific neutralization coefficient of the present invention, compared with the polymer which is produced by a conventional post-neutralization, has a superior quality in mixing uniformly with the surface crosslinking agent.

In the described manufacturing method, after the polymer and the crosslinking agent are mixed together, heat-treatment is carried out as required in accordance with the type of the crosslinking agent used so as to crosslink the vicinity of the polymer surface. It is preferable that the temperature of the heat-treatment, although it depends on types of the surface crosslinking agent, be not less than 80° C., more preferably in a range of 100° C. to 230° C., and even more preferably in a range of 160° C. to 220° C. When the temperature of the heat-treatment is less than 80° C., a long time is required for heat-treatment, and the productivity is lowered, and also a uniform crosslinking structure is not formed. This presents a possibility that the object of the present invention to provide a water-absorbent agent having a superior absorbing characteristic under pressure is not realized.

The heat-treatment is carried out by using a common drier or a heating oven. As the drier, for example, the following driers are available: a grooved mixing drier, a rotary drier, a disk drier, a fluidized bed dryer, an airborne dryer, an infra-red ray dryer, and other driers. It is preferable, although it depends on types of heat-treatment device such as the drier and the heating oven used for heat-treatment, that the heat-treatment time is 1 minute to 120 minutes, more preferably 5 minutes to 60 minutes.

The water-absorbent agent as obtained by the described manufacturing method is composed of a plurality of water-absorbent agent particles whose polymer particle surface is crosslinked, and the surface of the water-absorbent agent particles is crosslinked uniformly; thus, such a water-absorbent agent not only has high absorbency under no applied pressure but also has improved absorbency under applied pressure so that even under a high pressure of 50 g/cm$^2$, superior absorbency, for a saline solution, of not less than 20 g/g, preferably not less than 23 g/g, more preferably not less than 25 g/g, even more preferably not less than 27 g/g, and most preferably not less than 30 g/g is exhibited. Also, the water-absorbent agent as obtained by the described manufacturing method contains a small amount of water soluble component of not more than 10 percent by weight, more preferably not more than 5 percent by weight.

As described, in order to obtain a water-absorbent agent having high absorbency under no applied pressure and under high pressure wherein the amount of water soluble component is lower than the conventional water-absorbent agent, it is required to carry out post-neutralization. In the present invention, the ideal value of the lower limit of the neutralization coefficient is 0. However, in order to obtain an ideal neutralization coefficient value of 0 from the polymer which is obtained by post-neutralization process, for example, a large mixer or high speed mixing which induces a high load on the product is required. This might result in a high cost overall and a problem of damaging the product. Therefore, in order to achieve the objects of the present invention, considering that whether the effect obtained by making the neutralization coefficient 0 is worth the downsides, usually, the lower limit of the neutralization coefficient of the product water-absorbent agent of 1 is sufficient. Also, since the neutralization state is maintained even after the crosslinking reaction, the neutralization coefficient of the final water-absorbent agent is the same as the neutralization coefficient of the polymer particles during the crosslinking reaction. Thus, the resulting water-absorbent agent has (a) the first neutralization coefficient in a range of not less than 1 and not more than 10, more preferably in a range of not less than 0 and not more than 10, and/or (b) the second neutralization coefficient in a range of not less than 1 and not more than 30, more preferably in a range of not less than 0 and not more than 30, and (c) absorbency for a saline solution under the load of 50 g/cm$^2$ of 20 g/g.

Note that, in the water-absorbent agent obtained by polymerizing the acid group containing monomer which has been neutralized beforehand to a desirable neutralization ratio, since the acid group containing monomer already has a desirable neutralization ratio, the neutralization coefficient, both the first and second, becomes 0. However, in the case where the acid group containing monomer which has been neutralized beforehand to a desirable neutralization ratio is polymerized, it is difficult to obtain a water-absorbent agent whose water soluble component is reduced.

Thus, in order to stably obtain a water-absorbent agent having a reduced water soluble component and high absorbency, it is required, as described, to (1) carry out post-neutralization and (2) control at the particle level the neutralization ratio of the polymer obtained by neutralizing the hydrogel polymer constituting the water-absorbent agent.

The water-absorbent agent in accordance with the present invention has high absorbency under no applied pressure as well as under high pressure, and is provided with a liquid guiding space for allowing an absorbed fluid to be transported towards the inside of the water-absorbent agent under any conditions, with or without applied pressure. Thus, the present water-absorbent agent can be suitably adopted, together with a supporting structure made of a hydrophilic fibrous material such as paper and crushed pulp, as sanitary articles for an extended period of time.

Also, in a 100 times swollen gel which is prepared by swelling with water by 100 times the dead weight of the water-absorbent agent of the present invention, a change in pH between elapsed time of 5 minutes and 120 minutes after the formation of the 100 times swollen gal is significantly small, not more than 0.2. Namely, when the pH of the 100 times swollen gel after elapsed time of 5 minutes is $Y_1$, and the pH of the 100 times swollen gel after elapsed time of 120 minutes is $Y_2$, the following relation is satisfied:

$$Y_1 - Y_2 \leq |0.2|$$

Thus, in sanitary articles adopting the water-absorbent agent of the present invention, the amount of residual alkali and acid used for neutralization is small, and even when an aqueous liquid such as body fluid is absorbed, a stable pH is maintained, and compared with the conventional water-absorbent agent, safety is improved.

As described, in the manufacturing method of the water-absorbent agent of the present invention, the neutralization ratio of each of the polymer particles which are prepared from polymer obtained through neutralization of the hydrogel polymer produced by polymerizing the monomer component including the acid group containing monomer (salt) is controlled to have an allowable neutralization ratio so as to stably obtain a water-absorbent agent having high absorbency under no applied pressure and under high pressure (load) wherein the amount of water soluble component is smaller than the conventional water-absorbent agent, and the pH of the swollen gel is small. Note that, in the case where the water-absorbent agent is to be manufactured without controlling the neutralization ratio of the polymer particles, it is difficult to stably obtain a water-absorbent agent having superior absorbing characteristics. Also, in the case where the neutralization coefficient of the water-absorbent particles constituting the product water-absorbent agent is not controlled, when the water-absorbent agent is swollen with an aqueous liquid to form a swollen gel, by the residual acid and alkali used for neutralization remaining in the water-absorbent agent, neutralization gradually proceeds in the gel, thus presenting a problem of safety and instable pH. Therefore, from this point of view, it can also be seen that the water-absorbent agent manufactured by the described method can be safely adopted as a water-absorbent agent of sanitary articles and other products for an extended period of time.

Also, by measuring (confirming) the neutralization coefficient of the mass of the polymer particles while controlling the neutralization ratio of the polymer particles, the end point of neutralization of hydrogel polymer can be estimated for stably obtaining the water-absorbent agent having superior absorbing characteristics, thus allowing the hydrogel polymer to be uniformly neutralized at the particle level in a shorter period of time. As a result, it is possible to stably obtain the water-absorbent agent having superior absorbency in even shorter period of time.

Thus, in order to obtain the water-absorbent agent of the present invention, it is preferable to carry out a crosslinking process after confirming that the neutralization coefficient of the polymerized polymer is not more than a predetermined value. However, as mentioned above, the neutralization coefficient can also be used as an estimate of the end point of neutralization of the hydrogel polymer. Thus, for example, when manufacturing the water-absorbent agent for the first time, by confirming the condition satisfying the requirement for the neutralization coefficient, and by carrying out neutralization in accordance with the confirmed condition, it is possible to skip the confirming step of the neutralization coefficient in the following manufacturing of the water-absorbent agent. Namely, in the present invention, the mass of the polymer particles is neutralized until the neutralization coefficient thereof is not more than a predetermined value so as to stably obtain a water-absorbent agent in which each of the water-absorbent agent particles constituting the water-absorbent agent is controlled to have an allowable neutralization ratio.

In the water-absorbent agent of the present invention, for example, in water-absorbent articles such as paper diapers and sanitary napkins, which are manufactured by combining the water-absorbent agent and a fibrous material, even when used under a high concentration condition wherein a proportion of the water-absorbent agent in the sum of the water-absorbent agent and the fibrous material such as pulp is not less than 50 percent by weight, clogging of capillary under load is not induced. Therefore, with the present water-absorbent agent, it is possible to provide an absorbent and water-absorbent articles exhibiting superior diffusivity for a long period of time with a low occurrence of leakage. As described, the water-absorbent agent of the present invention efficiently exhibits the water absorbing ability even when adopted as a thin absorbent containing a high concentration of water-absorbent agent, thus suitably adopted as an absorbent in thin sanitary articles.

Also, in the present invention, as a method for stably obtaining a water-absorbent agent having superior absorbency wherein each of the water-absorbent agent particles constituting the water-absorbent agent is controlled so as to have an allowable neutralization ratio, it is possible to adopt a method including the steps of post-neutralizing the hydrogel polymer; heat-treating the resulting polymer in a gel state while maintaining the water content of the polymer within a predetermined range; reducing the water content of the polymer so as to dry the polymer; and allowing the resulting polymer to react with the crosslinking agent.

As a conventional example, for example, the aforementioned applications disclose water-absorbent resin which is produced by neutralizing a hydrogel polymer obtained by polymerization of a monomer component including acrylic acid (salt), and thereafter crosslinking the hydrogel polymer with a crosslinking agent. However, these publications are silent about neutralizing the hydrogel polymer, heat-treating the resulting polymer (neutralized gel), drying the polymer, and then applying a surface crosslinkage to the polymer. Indeed, heating and stirring of the neutralized gel are avoided in these patents because it was thought that heating and stirring would deteriorate the polymer.

Namely, since it is known that a polymer is thermally and mechanically deteriorated by heating and stirring of hydrogel polymer, after the end point of neutralization as determined by the conventional practice, namely after confirming using an indicator such as phenolphthalein that the base has been consumed, in order to avoid deterioration and to improve productivity, heating and stirring of polymer (neutralized gel) after neutralization is not carried out.

However, in the study made by the inventors of the present invention, in the case where the neutralized gel was allowed to react with the crosslinking agent after the neutralized gel was subjected to heat-treatment and was dried, even when the water soluble component of the product water-absorbent agent is increased, compared with a conventional method in which a water-absorbent agent is obtained by polymerizing a monomer component whose main component is acrylic acid which has been neutralized beforehand, it was found that the water-soluble component is reduced, and surprisingly, the absorbency under no applied pressure and under high pressure is increased.

Also, in the study made by the inventors of the present invention, in the case where the neutralized gel was allowed to react with the crosslinking agent without carrying out heat-treatment, it was found that it is difficult to increase the absorbency of the product water-absorbent agent under high pressure to a certain level, and that a water-absorbent agent having superior absorbing characteristic such as absorbency under high pressure cannot be stably obtained. Also, even when the neutralized gel was subjected to heat-treatment, when the product polymer is not allowed to react with a crosslinking agent which is reactive to the functional group of the polymer, and when the crosslinking agent is not added to the dried polymer, it was found that it is difficult to increase the absorbency of the product water-absorbent agent under high pressure to a certain level, and that a water-absorbent agent having superior absorbing characteristic such as absorbency under high pressure cannot be stably obtained.

In the described manner, in the case of adopting a method in which the neutralized gel is subjected to heat-treatment and is dried before crosslinking the neutralized gel, it is preferable that the hydrogel polymer used for neutralization is a large gel whose maximum diameter is at least 1 cm, more preferably not less than 2 cm, even more preferably not less than 3 cm, and most preferably not less than 5 cm. Also, it is preferable that the temperature of hydrogel polymer when neutralizing the hydrogel polymer be in a range of 40° C. to 100° C., more preferably in a range of 60° C. to 90° C.

The large gel is obtained by the static polymerization (partially static polymerization or completely static polymerization), and the upper limit of the size of the large gel is determined appropriately by the polymerization method and the scale. However, usually, it is preferable that the maximum diameter thereof be not more than 200 cm, more preferably not more than 100 cm, and most preferably not more than 50 cm. In the case where the size of the hydrogel polymer after polymerization is outside this range, neutralization is carried out after the hydrogel polymer is roughly chopped into small particles as required so that the maximum diameter of the particles is 1 cm to several 10 cm.

When neutralizing the large gel or the chopped gel, a basic substance is added to the gel, and the gel is pulverized simultaneously with neutralization. Here, it is preferable that the large gel or the chopped gel are finely pulverized so that the diameter resulting particles is not more than 5 mm, more preferably not more than 2 mm, even more preferably in a range of 0.2 mm to 2 mm. The finely pulverized gel may be kneaded and integrated. For pulverization, a kneader or a perforated panel-equipped plodder such as a variety of gel cutters and meat choppers is used.

Note that, as disclosed in U.S. Pat. No. 4,985,514, in the case of post-neutralizing the hydrogel polymer after finely pulverizing the hydrogel polymer to have a diameter of not more than 5 mm, there is a case where absorbency under applied pressure is not increased by the above-described method. Thus, when adopting, as a manufacturing method of the water-absorbent agent, a method in which the neutralized gel is subjected to heat-treatment and is dried before crosslinking the hydrogel polymer, it is preferable to add a basic substance to an unpulverized statically polymerized gel having a maximum diameter of not more than 1 cm, and carry out pulverization simultaneously with neutralization until coloration by phenolphthalein disappears, and it is more preferable to continue pulverizing and stirring even after neutralization. In the case where static polymerization is not carried out or the size of the hydrogel polymer does not fall in the above-mentioned range, absorbency under applied pressure is not increased sufficiently.

In the case of adopting the method in which the neutralized gel is subjected to heat-treatment and is dried before crosslinking the neutralized gel, the method for neutralizing the hydrogel polymer is not particularly limited. For example, it is possible to adopt a method in which a neutralizer or an aqueous solution of the neutralizer is added and kneaded while chopping the hydrogel polymer in a container having a plurality of rotation shafts by the shearing force exerted by the rotation of the rotation shafts (Japanese Publication for Unexamined Patent Application No. 131209/1989 (Tokukaihei 1-131209)). In the present invention, in the case of adopting the method in which the neutralized gel is subjected to heat-treatment and is dried before crosslinking the neutralized gel, it is assumed that the end point of neutralization has been reached when all the neutralizer have been absorbed by the hydrogel polymer and when it is confirmed that the base has been consumed as indicated by the indicator such as phenolphthalein.

When adopting the described method, it is possible to carry out neutralization in accordance with the described methods (1) through (12). In the case of adopting the method (1), it is preferable that the amount of aqueous liquid to be added for neutralization of the hydrogel polymer, with respect to 100 parts by weight of the hydrogel polymer, be in a range of 2 parts by weight to 100 parts by weight, more preferably in a range of 5 parts by weight to 100 parts be weight, and even more preferably in a range of 10 parts by weight to 50 parts by weight. When the added amount of the aqueous liquid is less than 2 parts by weight, the time required for neutralization is extended, and the absorbency under high pressure might not increase even when a crosslinking agent is added to polymer particles obtained by applying a heat-treatment to the neutralized hydrogel polymer (neutralized gel) and drying the polymer. On the other hand, when the added amount of the aqueous liquid exceeds 100 parts by weight, it becomes difficult to dry the polymer, and too much weight is put on the drying process for finishing the product, and the properties of the product water-absorbent resin are poor, thus industrially not preferable.

When adding the aqueous liquid during neutralization of the hydrogel polymer, it is preferable to mix and knead the aqueous liquid and the hydrogel polymer continuously or discontinuously. Also, after stopping the heating of the neutralized gel, it is possible to dry the neutralized gel after maintaining the neutralized gel, with or without insulation, for not less than 2 hours, more preferably not less than 6 hours, and even more preferably not less than 12 hours. It is preferable that the maintaining temperature of the neutralized gel after heat-treatment be in a range of 0° C. to 80° C., and more preferably in a range of 5° C. to 50° C. without a change in the water content of the hydrogel polymer.

When adopting the described method, after post-neutralizing the hydrogel polymer, it is required that the product neutralized gel is subjected to heat-treatment and is dried.

In the heat-treatment of neutralized gel, the hydrogel polymer is neutralized until coloration by phenolphthalein disappears, and thereafter resulting neutralized gel is maintained in a gel state with heat for a certain period of time. The heat-treatment of the neutralized gel is carried out before drying, preferably, by heating the neutralized gel while substantially maintaining the solid component of the neutralized gel. It is preferable that the solid component of the neutralized gel during heat-treatment be in a range of 10 percent by weight to 70 percent by weight, and heat-treatment is carried out so that (i) for example, by adding an aqueous liquid as required, a change in concentration of the solid component of the neutralized gel is in a range of not more than ±30 percent by weight, more preferably in a range of not more than ±20 percent by weight, even more preferably in a range of not more than ±10 percent by weight, and most preferably in a range of not more than ±5 percent by weight, or (ii) the solid component of the neutralized gel is in a range of 10 percent by weight to 70 percent by weight. Preferably, heat-treatment is carried out so as to satisfy the conditions of both (i) and (ii).

Namely, heat-treatment of the neutralized gel is carried out in a gel state for a certain period of time while maintaining the solid component of the polymer in a range of 10 percent by weight to 70 percent by weight, more preferably in a range of 15 percent by weight to 55 percent by weight, even more preferably in a range of 20 percent by weight to 40 percent by weight. Note that, in the present invention, the water content of the neutralized gel is the amount which is obtained by extracting the solid component from the weight of the neutralized gal.

Also, it is preferable that the heating time for the neutralized gel be in a range of 0.2 hours to 10 hours, more preferably in a range of 0.3 hours to 5 hours, and even more preferably in a range of 0.5 hours to 4 hours. Also, when heating the neutralized gel, it is preferable that the neutralized gel is maintained at a temperature of not less than 50° C., more preferably in a range of 65° C. to 130° C., and even more preferably in a range of 75° C. to 100° C. Although, heating temperature may be adjusted by adding salts or a solvent other than water or by adjusting the pressure, when the heating temperature is low, the effect of the present invention may not be obtained, and when the heating temperature is too high, the water-absorbent resin may deteriorate.

Also, when subjecting the neutralized gel to heat-treatment, it is preferable that heating be carried out simultaneously with stirring and it is more preferable, in order to achieve the objects of the present invention, to pulverize and knead the neutralized gel simultaneously with stirring thereof. Also, in order to promote pulverization and kneading, the neutralized gel may be compressed mechanically. The rotation speed of the stirring vane or the rotation shafts for stirring the neutralized gel is not particularly limited; however, it is preferable that the rotation speed is in a range of 1 rpm to 1000 rpm, more preferably in a range of 10 rpm to 500 rpm.

In the present invention, in the case of adopting the described method, it is preferable that the device to be used for neutralization and heat-treatment is capable of generating a large shearing force. The mixing device is not particularly limited so that, for example, as a mixing device for mixing the neutralized polymer and the surface crosslinking agent, it is possible to adopt the above-mentioned mixing device. Also, the heat-treatment is carried out preferably by an external heat so as to maintain the temperature of the neutralized gel within the above-mentioned range. Thus, it is preferable that the mixing device is capable of external heating using, as a heat source, a jacket, a hot air, an IR ray, and a micro wave, etc. Also, the mixing device to be used for neutralization and a heat-treatment device for carrying out heat-treatment after neutralization may be a single device or separate devices; however, it is preferable that the heat-treatment device is also provided with stirring function, and has a structure for carrying out pulverization and kneading.

Also, a method for drying the polymer (neutralized gel) after heat-treatment is not particularly limited so that a variety of conventionally known drying methods such as hot-air drying, thin-film drying using a drum dryer, reduced-pressure drying, fluid bed drying, and freeze drying may be adopted. The drying temperature for drying the polymer is not particularly limited; however, a temperature in a range of substantially 80° C. to 230° C. is adopted. Also, a pulverizing method is not particularly limited so that, for example, a variety of conventionally known pulverizing methods such as a method using a hammer granulator, a roll granulator, or a jet-air granulator may be adopted. Also, in the described method, in drying process, the neutralized gel is pulverized so that the solid component thereof is particles of not less than 80 percent, preferably not less than 90 percent, and more preferably not less than 95 percent.

In the present invention, when carrying out heat-treatment, the water soluble component may be increased, in addition to heating, by stirring, kneading, and pulverizing of the neutralized gel. However, compared with the method in which the water-absorbent agent is obtained by polymerizing a monomer component whose main component is acrylic acid, etc., which has been neutralized beforehand, the water soluble component of the water-absorbent agent as obtained by the described method is much smaller. A change in amount of the water soluble component can be determined with ease by comparing a difference between (a) the amount of water soluble component (percent by weight) in a polymer obtained by drying the neutralized gel which has been heat-treated and (b) the amount of water soluble component in a neutralized gel which has not been heat-treated.

Although the amount of water soluble component in the dried polymer may or may not be reduced by the heat-treatment of the neutralized polymer, preferably, by carrying out heat-treatment so as to increase the amount of water soluble component in a range of 0.05 percent by weight to 20 percent by weight, more preferably in a range of 0.1 percent by weight to 10 percent by weight, or even more preferably in a range of 0.2 percent by weight to 5 percent by weight, it is possible to stably obtain a water-absorbent agent having superior absorbency under high pressure. Note that, when increasing the amount of water soluble component in the dried polymer by heat-treatment, in order to confine the amount within the amount of water soluble component of the target dried polymer, polymerization conditions are adjusted beforehand appropriately. For example, the amount of inner crosslinking agent used is increased.

However, in the case where the amount of water soluble component after heat-treatment is too large, there is a case where the objects of the present invention are not achieved. Thus, when increasing the amount of water soluble component in the dried polymer by heat-treatment, it is preferable to heat-treat the neutralized gel so that the final amount of water soluble component in the dried polymer is not more than 20 percent by weight, preferably not more than 15 percent by weight, more preferably not more than 10 percent by weight. The amount of water soluble component after heat-treatment is suitably adjusted in accordance with conditions for heat-treatment (temperature, time, and presence or absence of stirring) and crosslinking density of neutralized gel before heat-treatment.

By the heat-treatment of neutralized gel, in the case where the amount of water soluble component in the dried polymer and the amount of the water soluble component increased by the heat-treatment are outside the above range, absorbency under low pressure (for example 20 g/cm$^2$) is increased to a certain level; however, there is a case where absorbency under high pressure (for example 50 g/cm$^2$) is not increased to a certain level.

One of the reasons for the increase in absorbency under high pressure (for example 50 g/cm$^2$) by heat-treatment of the neutralized gel is that by the heat-treatment of the neutralized gel, uniform neutralization is promoted at the particle level. Namely, it is speculated that when the above method is adopted, because the amount of water soluble component is generally increased, rearrangement of the polymer structure of the water-absorbent resin is induced by heat-treatment, and as a result, the following step of adding a crosslinking agent to the dried polymer is affected positively. Indeed, when adopting the above method, even when the neutralization ratio of the neutralized gel does not satisfy the above-mentioned requirement for the neutralization coefficient at the time of confirming the end point of the neutralization of the neutralized gel, when the neutralization ratio of the polymer which is obtained by drying is measured after the neutralized gel is heat-treated, it was found that the neutralization coefficient of the polymer satisfied the requirement for the neutralization coefficient.

Although the polymer after heat-treatment, provided that the polymer is in a dried state (powder), may be allowed to react with a crosslinking agent without adjusting the water content, in order to maximize the absorbing characteristic of the final product under high pressure, it is preferable to adjust the water content of the polymer to not more than 10 percent by weight, pulverize and adjust the resulting polymer to have a desired particle size as required, and then add the crosslinking agent to perform the reaction.

As described, the water-absorbent agent of the present invention is obtained by subjecting the neutralized gel to heat-treatment, and the neutralized gel is dried and pulverized to a powder, thereafter resulting polymer as a precursor of the absorbent agent is reacted with a crosslinking agent which is reactive to the functional group of the polymer so as to carry out surface crosslinkage.

The polymer as a precursor of the water-absorbent agent is a powder of a discrete particle or an aggregate, and takes a variety of shapes such as an irregular crushed shape, a spherical shape, an irregular granular shape, a rod shape, a substantially spherical shape, and a flat shape. It is preferable that the water content of the polymer be not more than 10 percent by weight, more preferably not more than 7 percent by weight, and even more preferably not more than 5 percent by weight. Also, it is preferable that the average particle diameter of the polymer particles obtained by pulverizing and classifying the dried polymer is in a range of 200 μm to 600 μm, and more preferably, the proportion of particles having a diameter of not more than 150 μm is not more than 10 percent by weight, even more preferably the proportion of particles having a diameter of not more than 150 μm is not more than 5 percent by weight.

The method for surface-crosslinking the polymer as a precursor of the water-absorbent agent is not particularly limited so that the described method can be adopted.

As described, in the present invention, the polymer (neutralized gel) after neutralization is subjected to heat-treatment, and is processed in the presence of a crosslinking agent after drying so as to carry out surface crosslinkage, thus making the crosslinking density in a vicinity of the surface of the polymer sufficiently higher than the inside thereof. As a result, a water-absorbent agent having superior absorbency is realized. Namely, when the water content of the polymer before adding a surface crosslinking agent is high, the surface crosslinking agent spreads inside the polymer, resulting in low absorbency under no applied pressure and under high pressure. Particularly, as in the conventional practice, in the case where a cross linking agent is added to a hydrogel polymer before drying, even when the neutralized gel is subjected to heat treatment before drying after addition of the crosslinking agent, although the amount of water soluble component is lowered to some degree, absorbency under applied pressure and under high pressure is low, and the objects of the present invention is not realized.

In the water-absorbent agent obtained by the described method in which the neutralized gel is subjected to heat-treatment and is dried before carrying out cross linkage, absorbency under no applied pressure for synthetic urine is not less than 40 g/g, more preferably not less than 45 g/g, and even more preferably not less than 50 g/g, and also the absorbency under high pressure and the amount of water soluble component are superior. Further, in the water-absorbent agent obtained by the described method, the amount of water soluble component is significantly low, not more than 20 percent by weight, preferably not more than 15 percent by weight, even more preferably not more than 10 percent by weight, and most preferably not more than 5 percent by weight. Moreover, in the above water-absorbent agent, since the cross linking reaction proceeds uniformly on the surface, a water absorbing characteristic under pressure is improved, and superior absorbency for a saline solution is exhibited even under a high pressure (high load) of 50 g/cm², such that the absorbency is not less than 20 g/g, preferably not less than 23 g/g, more preferably not less than 25 g/g, even more preferably not less than 27 g/g, and most preferably not less than 30 g/g. Also, the above water absorbent agent shows remarkably high absorbency for synthetic urine, such that the absorbency is preferably not less than 25 g/g, more preferably not less than 30 g/g, even more preferably not less than 35 g/g, and most preferably not less than 39 g/g.

As described, in the described manufacturing method of the water-absorbent agent, the water-absorbent agent particles constituting the water-absorbent agent are individually controlled so as to have an allowable neutralization ratio, thus stably providing a water-absorbent agent having high absorbency under no applied pressure and under high pressure (load), wherein the amount of water soluble component is lower than that of the conventional water-absorbent agent.

Also, in the described manufacturing method of the water-absorbent agent, the neutralization ratio of the polymer particles when reacted to the cross linking agent is individually controlled in a short period of time of several ten minutes to several hours, thus obtaining a water-absorbent agent composed of a plurality of water-absorbent agent particles wherein the surface of the polymer particles are crosslinked, and the neutralization ratio of the water-absorbent agent particles are individually controlled. Hence, with the described method, it is possible to provide a manufacturing method of the water-absorbent agent having high absorbency under no applied pressure and under high pressure, wherein the amount of water soluble component is lower than that of the conventional water-absorbent agent.

Also, in the water-absorbent agent obtained by the described method, since the neutralization ratio is controlled, neutralization is uniform at the particle level. Therefore, even when the water-absorbent agent take a form of a swollen gel, the amount of residual alkali and acid in the water-absorbent agent is small, and a change in pH is also small, thus having a superior safety.

Also, in the water-absorbent agent obtained by the described method, absorbency under no applied pressure and under high pressure is high, and a liquid guiding space is provided for allowing an absorbed fluid to be transported towards the inside of the water-absorbent agent under any conditions, with or without applied pressure. Thus, the present water-absorbent agent can be suitably adopted, together with a supporting structure made of a hydrophilic fibrous material such as paper and crushed pulp, as sanitary articles for an extended period of time. For example, in water-absorbent articles, such as paper diapers and sanitary napkins, which are made by combining the water-absorbent agent and a fibrous material, even when such water-absorbent articles were used under a high concentration condition wherein a proportion of the water-absorbent agent in the sum of the water-absorbent agent and the fibrous material such as pulp is not less than 50 percent by weight, clogging of capillary under load is not induced.

Therefore, with the present water-absorbent agent, it is possible to provide an absorbent and water-absorbent articles exhibiting superior diffusivity for a long period of time with a low occurrence of leakage. As described, the water-absorbent agent of the present invention efficiently exhibits the water absorbing ability even when adopted as a thin absorbent containing a high concentration of water-absorbent agent, thus suitably adopted as an absorbent in thin sanitary articles using a large amount of water-absorbent agent.

For a fuller understanding of the nature and advantages of the invention, reference should be made to the ensuring detailed description taken in conjunction with the accompanying drawings.

PREFERRED EMBODIMENTS OF THE PRESENT INVENTION

The following will explain the present invention in detail in accordance with examples and comparative examples. However, the present invention is not limited to these examples. Note that, various properties of a water-absorbent agent were measured by the following methods.

(a) Absorbency Under Normal Pressure (No Load)

In order to measure absorbency of a water-absorbent agent under normal pressure, first, 0.2 grams of a water-absorbent agent was uniformly put into a pouch (60 mm×60 mm) made of nonwoven fabric, and was immersed in a saline solution (aqueous solution of 0.9 percent by weight of sodium chloride) or synthetic urine for 60 minutes at room temperature. After leaving it for 60 minutes, the pouch was taken out of the solution, and was subjected to centrifugation for 3 minutes under 250 G in a centrifuge to remove water, and the weight $W_1$ (g) of the pouch was measured. The same process was also carried out without using the water-absorbent agent, and the weight $W_0$ (g) was measured. The weight $W_1$ and the weight $W_0$ were then used to calculate absorbency (g/g) under normal pressure by the following equation.

Absorbency(g/g) Under Normal Pressure=(Weight $W_1$ (g)−Weight $W_0$ (g))/Weight of Water−Absorbent Agent(g)−1.

Also, in order to measure absorbency of polymer particles under normal pressure, the above method was adopted except that polymer particles were used instead of the water-absorbent agent.

As the synthetic urine, a solution in which 2.0 grams of KCl, 2.0 grams of $Na_2SO_4$, 0.85 grams of $NH_4H_2PO_4$, 0.15 grams of $(NH_4)_2HPO_4$, 0.19 grams of $CaCl_2$, and 0.23 grams of $MgCl_2$ are dissolved in 1 liter of ion exchanged water was adopted.

(b) Absorbency Under Applied Pressure (With Load)

Figure 1:
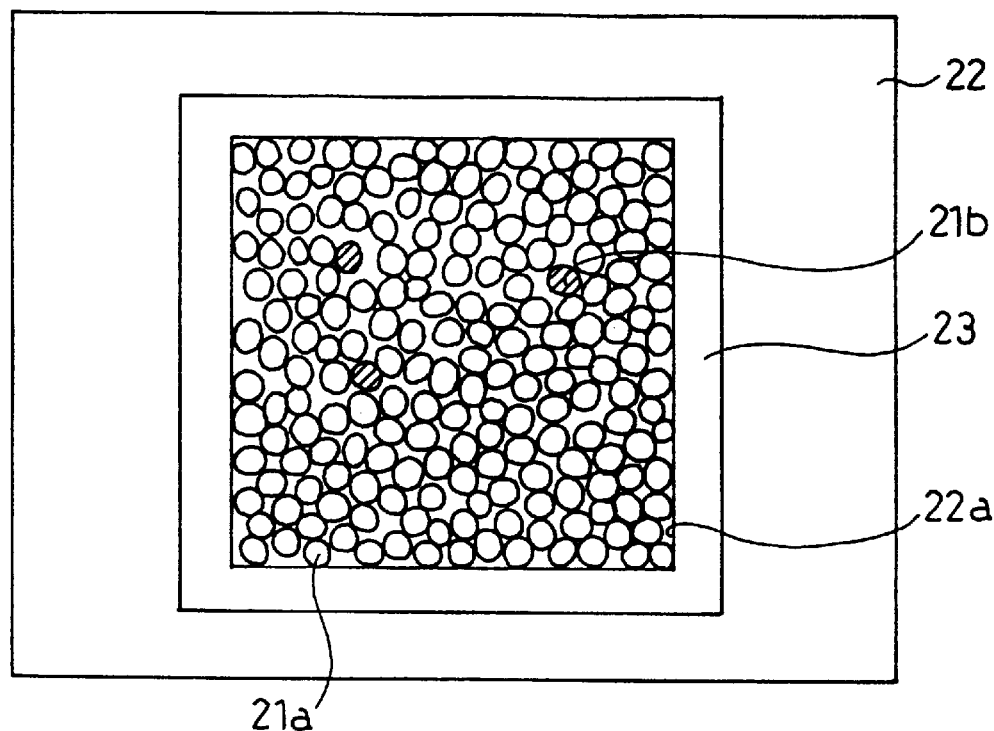
FIG. 1 is an explanatory drawing showing a neutralization state at a particle level of a hydrogel polymer adopted as a material for a water-absorbent agent of the present invention wherein the neutralization state are shown in a number of non-neutralized particles, having a non-first allowable neutralization ratio, contained in a plurality of polymer particles made from a polymer which is obtained through neutralization of the hydrogel polymer.
Figure 2:
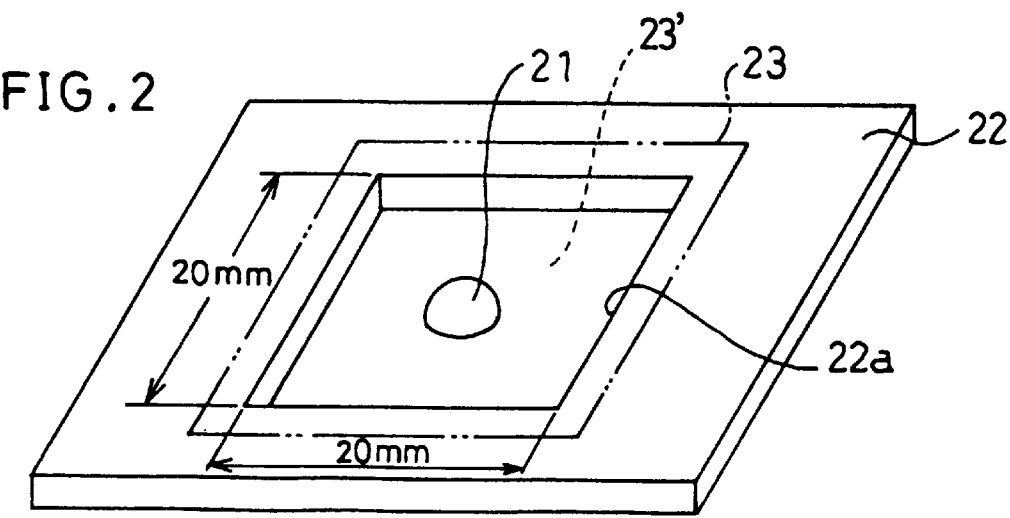
FIG. 2 is an explanatory drawing explaining a measuring method of a neutralization coefficient of the present invention.
Figure 3:
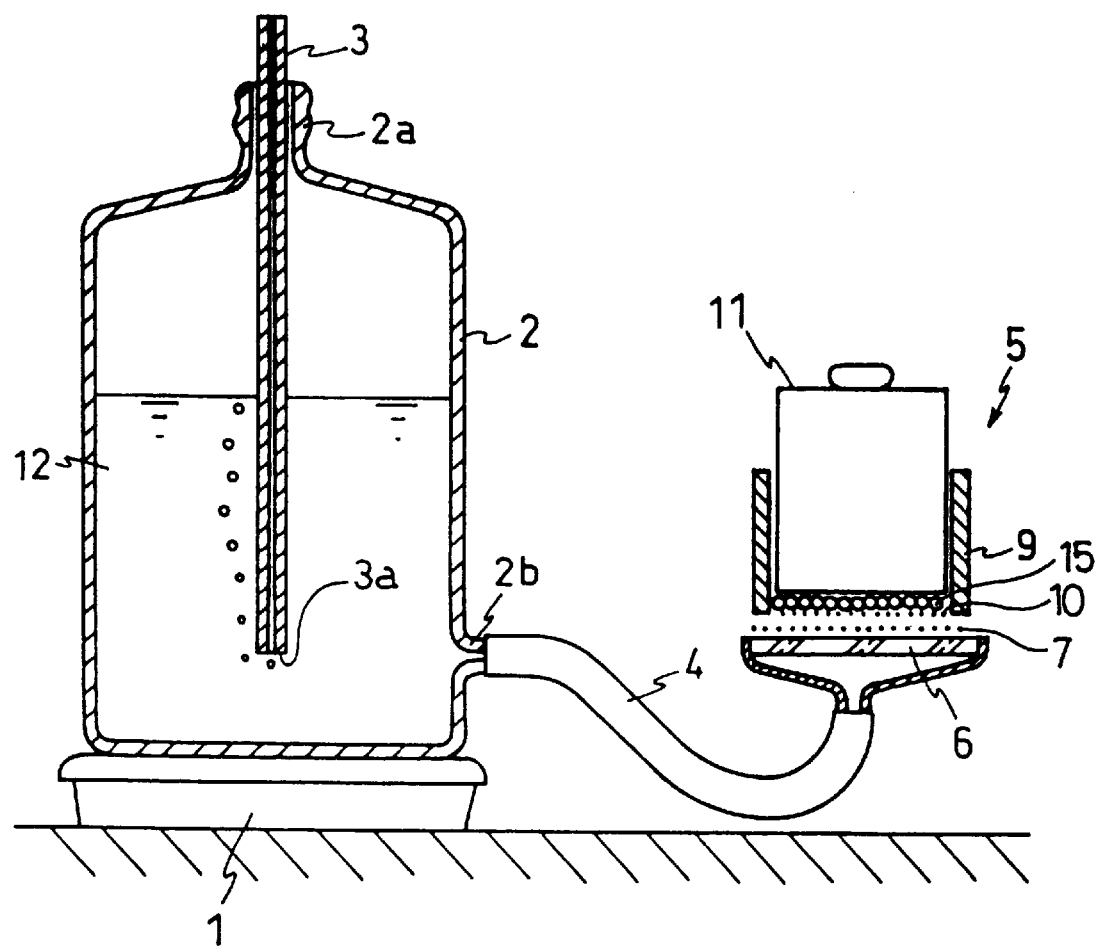
FIG. 3 is a cross sectional view schematically showing a measuring device used for a measurement of absorbency under applied pressure, which is one of the properties exhibited by the water-absorbent agent of the present invention.
Figure 4:
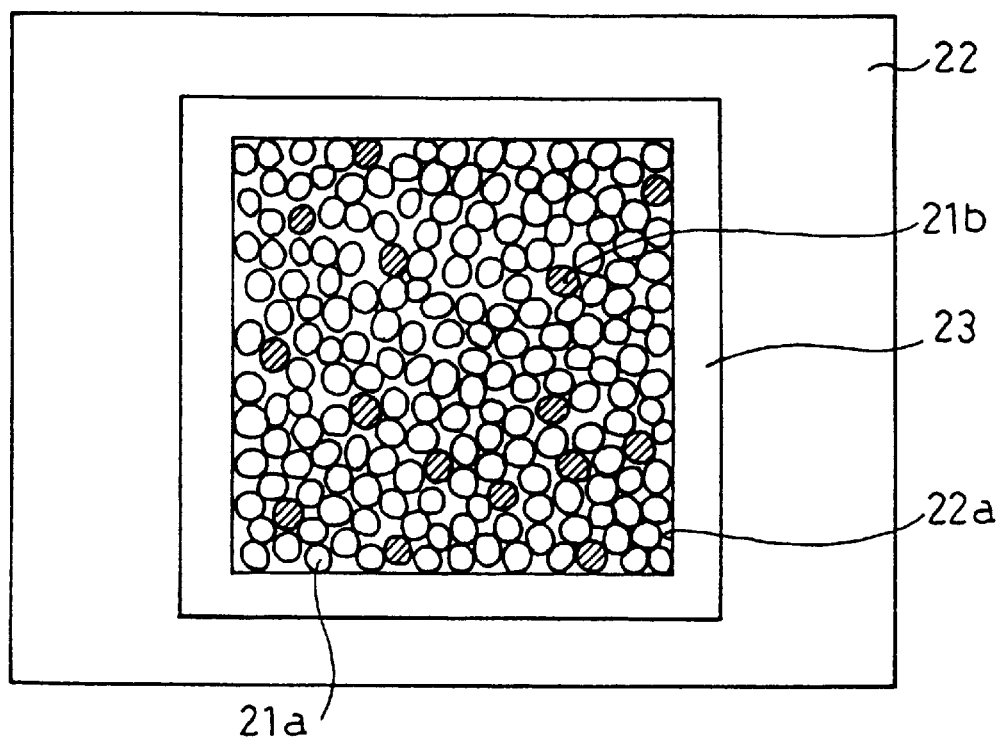
FIG. 4 is an explanatory drawing showing a neutralization state at a particle level of a conventional hydrogel polymer wherein the neutralization state are shown in a number of non-neutralized particles, having a non-first allowable neutralization ratio, contained in a plurality of polymer particles made from a polymer which is obtained through neutralization of the hydrogel polymer.

First, a measuring device to be used in the measurement of absorbency under applied pressure will be briefly explained referring to FIG. 3.

As shown in FIG. 3, the measuring device includes a balance 1, a container 2 of a predetermined volume placed on the balance 1, an air-intake pipe 3, a conduit 4, a glass filter 6, and a measuring section 5 placed on the glass filter 6.

The container 2 has an opening 2a on the top and an opening 2b on the side, and the air-intake pipe 3 is inserted through the opening 2a while the conduit 4 is fixed to the opening 2b. Also, the container 2 is filled with a predetermined amount of saline solution 12.

The lower end portion of the air-intake pipe 3 is dipped into the saline solution 12. The air-intake pipe 3 is provided for keeping the pressure in the container 2 substantially constant (atmospheric pressure).

The glass filter 6 has a diameter of 70 mm, and is connected to the container 2 through the conduit 4 made of silicon resin. Also, the relative position and height of the glass filter 6 to the container 2 are fixed. Namely, the glass filter 6 is fixed such that the upper surface thereof is slightly higher than the lower end surface 3a of the air-intake pipe 3.

The measuring section 5 is provided with a paper filter 7, a supporting cylinder 9, a metal gauze 10 which is attached to the bottom of the supporting cylinder 9, and a weight 11. In the measuring section 5, the paper filter 7 and the supporting cylinder 9 (i.e., metal gauze 10) are placed on the glass filter 6 in this order, and the weight 11 is placed on the metal gauze 10, that is, inside the supporting cylinder 9. The supporting cylinder 9 has an inner diameter of 60 mm, and the metal gauze 10 is made of stainless steel to have a 400-mesh (the size of each mesh is 38 $\mu$m). On the metal gauze 10, a predetermined amount of the water-absorbent agent 15 is uniformly dispersed. Also, the weight 11 can evenly apply load on the metal gauze 10 (i.e., on the water-absorbent agent 15).

The absorbency under applied pressure of water-absorbent agents of Example 1 through Example 4 and Comparative Example 1 through Comparative Example 3 were measured using the measuring device having the described arrangement. The following describes the measuring method.

First, the predetermined preparations ① and ② were made: ① the container 2 was filled with a predetermined amount of the saline solution 12, and ② the air-intake pipe 3 was inserted into the container 2. Then, the paper filter 7 was placed on the glass filter 6, and also 0.9 grams of the water-absorbent agent 15 was uniformly dispersed inside the supporting cylinder 9 (i.e., on the metal gauze 10). Thereafter, the weight 11 was placed on the water-absorbent agent thus dispersed.

Then, the metal gauze 10, i.e., the supporting cylinder 9 having the water-absorbent agent 15 and the weight 11 inside, was placed on the paper filter 7 in such a manner that the center of the supporting cylinder 9 is coincident with the center of the glass filter 6.

Next, the weight $W_2$ (g) the saline solution 12 absorbed by the water-absorbent agent 15 in 60 minutes since the supporting cylinder 9 was placed on the paper filter 7 was determined from a measured value read by the balance 1.

Then, absorbency (g/g) under applied pressure after 60 minutes since the start of absorption under applied pressure was calculated from the weight $W_2$ (g) and the weight (0.9 g) of the water-absorbent agent 15 by the following equation.

Absorbency Under Applied Pressure(g/g)=Weight $W_2$ (g)/Weight(g) of Water-Absorbent Agent Note that, in the measurement of absorbency under low pressure, a weight 11 having a load of 20 g/cm$^2$ was used, and in the measurement of absorbency under high pressure, a weight 11 having a load of 50 g/cm$^2$ was used.

Also, by using the described measuring device and the measuring method, the absorbency, for the saline solution 12 under high pressure, of water-absorbent agents and polymer particles of Examples 5 to 9 and Comparative Examples 4 to 6 were measured, and the absorbency thereof under high pressure were also measured by using the synthetic urine 12 instead of the saline solution 12. Note that, in the measurement of absorbency under high pressure, a weight 11 having a load of 50 g/cm$^2$ was used, and the absorbency of the polymer particles under pressure was measured by the method described above except that the polymer particles were used instead of the water-absorbent agent 15.

(c) Amount of Water Soluble Component 0.5 grams of water-absorbent agent was added to 1000 grams of deionized water, and after stirring for 16 hours, the solution was subjected to filtration with a filter. Then, 50 grams of filtrate obtained was transferred to a 100 ml beaker to which was added 1 ml of an aqueous solution of 0.1 N sodium hydroxide, 10 ml of an aqueous solution of N/200 methylglycolchitosan, and four drops of an aqueous solution of 0.1 percent toluidine blue. Thereafter, the amount of water soluble polymer component in the solution in the beaker was determined by colloidal titration using an aqueous solution of N/400 polyvinyl potassium sulfate. The titration amount A (ml) was obtained when the end point of the titration is reached as evidenced by turning of the color of the solution from blue to red purple. Also, the same process was carried out using 50 grams of deionized water instead of 50 grams of the filtrate so as to determine titration amount B (ml) as a blank. Then, the amount of water soluble component (per cent by weight) was calculated from the titration amount A and B thus obtained and a molecular weight C of the water-absorbent agent by the following equation.

Amount of Water Soluble Component (Percent by Weight)=(B−A)×0.01×C

(d) Change in pH

A beaker having a volume of 250 ml was filled with 198.00 grams of pure water (temperature of 23° C.±2° C.), and the pure water was stirred in a magnetic stirrer with a rotator having a length of 40 mm. Then, while stirring, 2.000 grams of water-absorbent agent was added at a time to the pure water which was then left untouched until all the pure water was uniformly gelatinized and the rotator stopped rotating. After the rotator stopped rotating, an electrode of a pH meter (glass electrode hydrogen ion concentration meter, provided by Horiba, Ltd.) which has been adjusted by a buffer solution was immediately inserted into the swollen gel in the beaker. Namely, the electrode was inserted into a substantially central portion of the 100 times swollen gel which has swollen 100 times the dead weight by absorption of water, and a pH value after elapsed time of 5 minutes $Y_1$ and a pH value after elapsed time of 120 minutes ($Y_2$) were read so as to calculate a change in pH by the following equation.

Change in pH=($Y_1$)−($Y_2$)

Note that, in the present invention, a larger change in pH indicates that (1) unreacted alkali (for example, sodium hydroxide as neutralizer) and (2) polyacrylic acid (generally weak acid) which has not been neutralized or has been weakly neutralized coexist in the water-absorbent agent, and as the powder of the water-absorbent agent form the 100 times swollen gel, neutralization gradually proceeds with time in the gel even after swelling. In other words, in the present invention, a larger change in pH indicates that the neutralization is incomplete in the water-absorbent agent before swelling, thus clearly indicating the presence of residual acid and alkali used in neutralization. Note that, the pH of water-absorbent agent, composed of monomers which have been neutralized beforehand, which is not subjected to post neutralization reaches equilibrium in substantially 5 minutes, and no further change in pH with time is observed.

(e) Water Content of Polymer particles 1.000 grams of polymer particles were placed in an aluminium cup (inner diameter of 53 mm×height of 23 mm), and were dried for 3 hours at 180° C. in an oven with no wind, and the dried weight was used to calculate the water content (per cent by weight) of the polymer particles.

EXAMPLE 1

A reaction liquid was prepared by mixing 720 grams of acrylic acid, 3.08 grams of N,N'-methylene-bis acrylamide (inner crosslinking agent), and 2718 grams of deionized water (solvent) in a reaction vessel which is a stainless-made twin arm type kneader with a lid and two sigma vanes equipped with a jacket having a volume of 10 liter. Then, while maintaining the temperature of the reaction liquid at 15° C., nitrogen replacement was carried out in the reaction vessel. Then, while stirring the blade of the kneader, as a polymerization initiator, 21.6 grams of a 2,2'-azobis(2-amidinopropane) dihydrochloride aqueous solution (10 percent by weight), 18.0 grams (1 percent by weight) of L-ascorbic acid aqueous solution, and 20.6 grams (3.5 percent by weight) of hydrogen peroxide aqueous solution were added to the reaction solution so as to start polymerization. Polymerization was carried out in such a manner that with the start of polymerization, the blade was stopped, and the temperature of the jacket was increased in accordance with the increase in temperature of the reaction solution so as to make the temperature of the jacket and the temperature of the reaction solution substantially the same. After the temperature of the reaction solution has reached a peak temperature, the temperature of the jacket was controlled so as to maintain the temperature of the reaction solution at not less than 55° C., and the reaction solution was matured for three hours. After the reaction, the blade was rotated, and resulting hydrogel crosslinked polymer was chopped into small particles so as to obtain particulate hydrogel crosslinked polymer (referred to as hydrogel polymer (A) hereinafter).

Then, while further pulverizing the hydrogel polymer (A) by rotation of the blade at a temperature of substantially 50° C., 750 grams (40 percent by weight) of sodium hydroxide aqueous solution as a neutralizer was dropped for 40 minutes and mixed. Thereafter, the blade was stopped, and after maintaining the mixed solution for 80 minutes at 50° C., 1 percent by weight of phenolphthalein-ethanol solution was added to resulting polymer. However, no red purple color of phenolphthalein was observed. Then, 400 grams of deionized water (aqueous liquid) was added and mixed with the polymer, and the mixed solution was maintained for 24 hours to finish the neutralization (neutralization ratio of 75 mole percent).

Then, the polymer after neutralization (referred to as polymer ($A_1$) hereinafter) was dried by a hot air of 50° C. for 16 hours, and the dried product was pulverized by a shaking mill and was classified so as to obtain polymer particles having a particle diameter of 150 μm to 850 μm (referred to as polymer particles ($A_1$) hereinafter) as a precursor of a water-absorbent agent. The water content of the polymer particles ($A_1$) was 8 percent by weight. A first neutralization coefficient and a second neutralization coefficient of the polymer particles ($A_1$) were measured by the afore-described method.

Thereafter, with respect to 100 parts by weight of the polymer particles ($A_1$), 0.5 part by weight of glycerol (first surface crosslinking agent), 0.05 part by weight of ethyleneglycol diglycidyl ether (second surface crosslinking agent), and an aqueous liquid composed of 3 parts by weight of water and 0.75 part by weight of isopropyl alcohol (hydrophilic organic solvent) were added and mixed, and the mixture was subjected to heat-treatment of 175° C. for 60 minutes so as to obtain a water-absorbent agent. The properties of the water-absorbent agent were measured by the afore-described method. Table 1 shows the results of the measurement along with the first and second neutralization coefficients of the polymer particles ($A_1$)

EXAMPLE 2

An unneutralized hydrogel polymer (A) was obtained by the same reactions and processes as in Example 1. The hydrogel polymer (A) was further chopped into small particles at 50° C., and 750 grams of sodium hydroxide aqueous solution (40 percent by weight) was dropped for 40 minutes and mixed. Thereafter, the blade was stopped, and after maintaining the mixed solution for 80 minutes at 50° C., 1 percent by weight of phenolphthalein-ethanol solution was added to resulting polymer. However, no red purple color of phenol phthalein was observed. Then, 400 grams of deionized water (aqueous liquid) was added and mixed with the polymer uniformly, and the mixed solution was rested for 5 days at room temperature to finish the neutralization (neutralization ratio of 75 mole per cent).

Then, the polymer after neutralization (referred to as polymer ($A_2$) hereinafter) was dried by a hot air of 50° C. for 16 hours, and the dried product was pulverized by a shaking mill for and was classified so as to obtain polymer particles having a particle diameter of 150 μm to 850 μm (referred to as polymer particles ($A_2$) hereinafter) as a precursor of a water-absorbent agent. The water content of the polymer particles ($A_2$) was 5 percent by weight. A first neutralization coefficient and a second neutralization coefficient of the polymer particles ($A_2$) were measured by the afore-described method.

Thereafter, with respect to 100 parts by weight of the polymer particles ($A_2$), 1 part by weight of propylene glycol (first surface crosslinking agent), 0.05 part by weight of ethyleneglycol diglycidyl ether (second surface crosslinking agent), and an aqueous liquid composed of 3 parts by weight of water and 0.75 part by weight of isopropyl alcohol were added and mixed, and the mixture was subjected to heat-treatment of 175° C. for 40 minutes so as to obtain a water-absorbent agent. The properties of the water-absorbent agent were measured by the afore-described method. Table 1 shows the results of the measurement along with the first and second neutralization coefficients of the polymer particles ($A_2$).

EXAMPLE 3

An unneutralized hydrogel polymer (A) was obtained by the same reactions and processes as in Example 1. The hydrogel polymer (A) was further chopped into small particles at 50° C., and 750 grams of sodium hydroxide aqueous solution (40 percent by weight) was dropped for 40 minutes and mixed. Thereafter, the blade was stopped, and after maintaining the mixed solution for 80 minutes at 50° C., 1 percent by weight of phenolphthalein-ethanol solution was added to resulting polymer. However, no red purple color of phenolphthalein was observed. Then, 400 grams of deionized water (aqueous liquid) was added and mixed with the polymer uniformly, and the mixed solution was rested for 12 hours at room temperature to finish the neutralization.

Then, the polymer after neutralization (referred to as polymer ($A_3$) hereinafter) was dried by a hot air of 50° C. for 16 hours, and the dried product was pulverized by a shaking mill and was classified so as to obtain polymer particles having a particle diameter of 150 μm to 850 μm (referred to as polymer particles ($A_3$) hereinafter) as a precursor of a water-absorbent agent. The water content of the polymer particles ($A_3$) was 8 percent by weight. A first neutralization coefficient and a second neutralization coefficient of the polymer particles ($A_3$) were measured by the afore-described method.

Thereafter, with respect to 100 parts by weight of the polymer particles ($A_3$), 1 part by weight of propylene glycol (first surface crosslinking agent), 0.05 part by weight of ethyleneglycol diglycidyl ether (second surface crosslinking agent), and an aqueous liquid composed of 3 parts by weight of water and 0.75 part by weight of isopropyl alcohol were added and mixed, and the mixture was subjected to heat-treatment of 175° C. for 40 minutes so as to obtain a water-absorbent agent. The properties of the water-absorbent agent were measured by the afore-described method. Table 1 shows the results of the measurement along with the first and second neutralization coefficients of the polymer particles ($A_3$).

EXAMPLE 4

An unneutralized hydrogel polymer (A) was obtained by the same reactions and processes as in Example 1. The hydrogel polymer (A) was further chopped into small particles at 50° C., and 750 grams of sodium hydroxide aqueous solution (40 percent by weight) was dropped for 40 minutes and mixed. Thereafter, the blade was stopped, and after maintaining the mixed solution for 80 minutes at 50° C., 1 percent by weight of phenolphthalein-ethanol solution was added to resulting polymer. However, no red purple color of phenolphthalein was observed. Then, 200 grams of deionized water (aqueous liquid) was added and mixed with the polymer uniformly, and the mixed solution was rested for 12 hours at room temperature to finish the neutralization.

Then, the polymer after neutralization (referred to as polymer ($A_4$) hereinafter) was dried by a hot air of 50° C. for 16 hours, and the dried product was pulverized by a shaking mill and was classified so as to obtain polymer particles having a particle diameter of 150 μm to 850 μm (referred to as polymer particles ($A_4$) hereinafter) as a precursor of a water-absorbent agent. The water content of the polymer particles ($A_4$) was 7 percent by weight. A first neutralization coefficient and a second neutralization coefficient of the polymer particles ($A_4$) were measured by the afore-described method.

Thereafter, with respect to 100 parts by weight of the polymer particles ($A_4$), 1 part by weight of propylene glycol (first surface crosslinking agent), 0.05 part by weight of ethyleneglycol diglycidyl ether (second surface crosslinking agent), and an aqueous liquid composed of 3 parts by weight of water and 0.75 part by weight of isopropyl alcohol were added and mixed, and the mixture was subjected to heat-treatment of 175° C. for 40 minutes so as to obtain a water-absorbent agent. The properties of the water-absorbent agent were measured by the afore-described method. Table 1 shows the results of the measurement along with the first and second neutralization coefficients of the polymer particles ($A_4$).

TABLE 1

|  | Examples | | | |
|---|---|---|---|---|
|  | 1 | 2 | 3 | 4 |
| First Neutralization Coefficient | 1 | 2 | 5 | 11 |
| Second Neutralization Coefficient | 1 | 2 | 9 | 16 |
| Absorbency (g/g) |  |  |  |  |
| Under Normal Pressure | 38 | 38 | 38 | 39 |
| Under Low Pressure | 34 | 36 | 33 | 34 |
| Under High Pressure | 26 | 27 | 26 | 25 |
| Water Soluble Component (%) | 1.7 | 1.3 | 1.4 | 2.1 |
| Change in pH | <0.1 | <0.1 | 0.17 | 0.15 |

Comparative Example 1

An unneutralized hydrogel polymer (A) was obtained by the same reactions and processes as in Example 1. The hydrogel polymer (A) was further chopped into small particles at 50° C., and 750 grams of sodium hydroxide aqueous solution (40 percent by weight) was dropped for 10 minutes and mixed. Thereafter, the blade was stopped, and after maintaining the mixed solution for 10 minutes at 50° C., 1 percent by weight of phenolphthalein-ethanol solution was added to resulting polymer. This time, clear red purple color of phenolphthalein was observed. Then, the polymer was rested for 1 hour at room temperature for neutralization so as to obtain a comparative polymer (referred to as polymer ($A_5$) hereinafter) (neutralization ratio of 75 mole percent).

Then, the polymer ($A_5$) was dried, pulverized, and classified by the same method as in Example 1 so as to obtain comparative polymer particles having a particle diameter of 150 μm to 850 μm (referred to as polymer particles ($A_5$) hereinafter) as a precursor of a water-absorbent agent. The water content of the polymer particles ($A_3$) was 8 percent by weight. A first neutralization coefficient and a second neutralization coefficient of the polymer particles ($A_5$) were measured by the afore-described method.

Thereafter, the polymer particles ($A_5$) were subjected to a surface crosslinking process by the same method as in Example 1 so as to obtain a comparative water-absorbent agent. The properties of the water-absorbent agent were measured by the afore-described method. Table 2 shows the results of the measurement along with the first and second neutralization coefficients of the polymer particles ($A_5$).

Comparative Example 2

An unneutralized hydrogel polymer (A) was obtained by the same reactions and processes as in Example 1. The hydrogel polymer (A) was further chopped into small particles at 50° C., and 750 grams of sodium hydroxide aqueous solution (40 percent by weight) was dropped for 40 minutes and mixed. Thereafter, the blade was stopped, and after maintaining the mixed solution for 80 minutes at 50° C., 1 percent by weight of phenolphthalein-ethanol solution was added to resulting polymer. However, no red purple color of phenolphthalein was observed. Then, the polymer was maintained for 24 hours at room temperature for neutralization without adding deionized water (neutralization ratio of 75 mole percent) so as to obtain a comparative polymer (referred to as polymer ($A_6$) hereinafter).

Then, the polymer ($A_6$) was dried, pulverized, and classified by the same method as in Example 1 so as to obtain comparative polymer particles (referred to as polymer particles ($A_6$) hereinafter) as a precursor of a water-absorbent agent having a particle diameter of 150 μm to 850 μm. The water content of the polymer particles ($A_6$) was 7 percent by weight. A first neutralization coefficient and a second neutralization coefficient of the polymer particles ($A_6$) were measured by the afore-described method.

Thereafter, the polymer particles ($A_6$) were subjected to a surface crosslinking process by the same method as in Example 1 so as to obtain a comparative water-absorbent agent. The properties of the water-absorbent agent were measured by the afore-described method. Table 2 shows the results of the measurement along with the first and second neutralization coefficients of the polymer particles ($A_6$).

Comparative Example 3

In the reaction vessel of Example 1, a reaction solution was prepared by dissolving 2.87 grams of polyethylene glycol diacrylate (other monomers) in 5367 grams of partially neutralized sodium acrylate aqueous solution (33 percent by weight) with a neutralization ratio of 75 mole percent. Then, while maintaining the temperature of the reaction solution at 26° C., nitrogen replacement was carried out in the reaction vessel. Thereafter, while stirring the reaction solution by the blade of the kneader, 12 grams of sodium persulfate aqueous solution (20 percent by weight) (polymerization initializer) and 10 grams of L-ascorbic acid aqueous solution (1 percent by weight) were added so as to polymerize and pulverize the gel for 60 minutes. As a result, particulate hydrogel crosslinked polymer (referred to as polymer (B) hereinafter) was obtained. 1 percent by weight of phenolphthalein-ethanol solution was then added to the polymer (B); however, no red purple color of phenolphthalein was observed.

Then, the polymer (B) was dried, pulverized, and classified by the same method as in Example 1 so as to obtain comparative polymer particles having a particle diameter of 150 μm to 850 μm (referred to as polymer particles (B) hereinafter) as a precursor of a water-absorbent agent. The water content of the polymer particles (B) was 6 percent by weight. A first neutralization coefficient and a second neutralization coefficient of the polymer particles (B) were measured by the afore-described method. Note that, as comparative particles, a crosslinked sodium polyacrylate having a neutralization ratio of not more than 55 mole percent was adopted.

Thereafter, the polymer particles (B) were subjected to a surface crosslinking process by the method of Example 1 so as to obtain a comparative water-absorbent agent. The properties of the water-absorbent agent were measured by the afore-described method. Table 2 shows the results of the measurement along with the first and second neutralization coefficients of the polymer particles (B).

TABLE 2

| | Comparative Examples | | |
|---|---|---|---|
| | 1 | 2 | 3 |
| First Neutralization Coefficient | 14 | 19 | 0 |
| Second Neutralization Coefficient | 36 | 41 | 0 |
| Absorbency (g/g) | | | |
| Under Normal Pressure | 40 | 40 | 39 |
| Under Low Pressure | 31 | 33 | 35 |
| Under High Pressure | 14 | 17 | 26 |
| Water Soluble Component (%) | 7.3 | 1.4 | 25 |
| Change in pH | 0.26 | 0.22 | <0.1 |

As it can be seen from the results in Table 1 and Table 2, the water-absorbent agents adopting the polymers obtained in the present Examples have high absorbency not only under no applied pressure (normal pressure) but also under low pressure and high pressure as well. It can also be seen from Table 1 and Table 2 that in the water-absorbent agents of the present Examples, the amount of water soluble components is lower than that of the water-absorbent agent adopting the polymers obtained in the Comparative Examples.

Also, because the neutralization coefficient of the polymer particles during crosslinking reaction is maintained in the water-absorbent agents as a final product, in the water-absorbent agents obtained in the present Examples, the neutralization ratio of the water-absorbent agent particles constituting the water-absorbent agent is controlled. Particularly, the polymer particles obtained in Examples 1 and 2 both satisfy the requirements for the first neutralization ratio and the second neutralization ratio, and the sum of (a) the number of polymer particles having a non-first allowable neutralization ratio and (b) the number of polymer particles having a neutralization ratio of not less than 95 mole percent is not less than 10 in 200 polymer particles. Also, from the results in Table 1, it can be seen that since the water-absorbent agents obtained in the present Examples are uniformly neutralized at the particle level, the change in pH with time while swelling is small, and safety is superior.

EXAMPLE 5

A reaction vessel is a twin arm type kneader with a lid and two sigma vanes equipped with a jacket having a volume of 2.5 liter whose inner surface is Teflon-coated. In the reaction vessel, a reaction solution was prepared by mixing 240.0 grams of acrylic acid, 769 mg (0.15 mole percent with respect to acrylic acid) of N,N'-methylene-bisacrylamide as an inner crosslinking agent, and 946.6 grams of deionized water as a solvent. Then, while maintaining the temperature of the reaction solution at 15° C., nitrogen replacement was carried out in the reaction vessel. Then, while stirring the reaction solution by the blade of the kneader, 7.2 grams of a 2,2'-azobis(2-amidinopropane) dihydrochloride aqueous solution as polymerization initializer (10 percent by weight), 3.0 grams of L-ascorbic acid aqueous solution (2 percent by weight), and 3.42 grams of hydrogen peroxide aqueous solution (7 percent by weight) were added to the reaction solution so as to start polymerization. Here, static adiabatic polymerization was carried out in such a manner that with the start of polymerization, the blade was stopped, and the temperature of the jacket was increased in accordance with the increase in temperature of the reaction solution so as to make the temperature of the jacket and the temperature of the reaction solution substantially the same. After the temperature of the reaction solution has reached a peak temperature, the temperature of the jacket was controlled so as to maintain the temperature of the reaction solution at not less than 55° C., and polymerization was carried out in the reaction solution for a total of one hour, thus obtaining hydrogel polymer (C).

After polymerization is finished, with respect to 1200 grams of unpulverized hydrogel polymer (C) having a maximum diameter of substantially 15 cm in the kneader, 180.4 grams (48 percent by weight) of sodium hydroxide aqueous solution (65 mole percent with respect to acrylic acid) was added at a time (within 10 seconds) from the upper portion of the kneader. This resulted in a two phase state in which an unabsorbed sodium hydroxide aqueous solution remained separately on the hydrogel polymer (C). Then, by rotating the blade of the kneader, a basic substance was added so as to neutralize and pulverize the unpulverized hydrogel polymer (C). As a result, the hydrogel polymer (C) was finely divided in substantially 10 minutes into irregular shaped particles, each having a diameter of not more than 10 mm, and no unabsorbed sodium hydroxide aqueous solution was observed with a naked eye. However, when 1 percent by weight of phenolphthalein-ethanol solution was directly added to the finely divided hydrogel polymer (C), a red purple color of phenolphthalein was still observed partially on the hydrogel polymer (C). When the blade was further rotated, after 40 minutes, the hydrogel polymer (C) was finely divided further into particles, each having a diameter of several mm (substantially 0.2 mm to 2 mm), and no red purple color of phenolphthalein was observed in each particle of the finely divided hydrogel polymer (C), and neutralization was finished. The neutralization ratio of hydrogel polymer after neutralization (referred to as neutralized gel ($C_1$) hereinafter) was 65 mole percent, and the solid content thereof was substantially 21 percent by weight.

Thereafter, the kneader was capped, and the neutralized gel ($C_1$) in the kneader was stirred in 30 rpm, and the temperature of the jacket was increased to 100° C. and the gel temperature was maintained at substantially 85° C. to 90° C., and while maintaining the solid content of 21 percent by weight, the neutralized gel ($C_1$) was subjected to heat-treatment for 3 hours. Then, the heat-treated neutralized gel ($C_1$) was taken out of the kneader, and was dried by a hot air of 160° C. for 65 minutes. Thereafter, the dried product was pulverized by a shaking mill and was classified by using a screen of JIS standard so as to obtain, as a precursor of a water-absorbent agent, polymer particles (referred to as polymer particles ($C_1$)), each having a diameter of 300 $\mu$m to 600 $\mu$m. The water content of the polymer particles ($C_1$) was 7 percent by weight. Also, the absorbency of the polymer particles ($C_1$) with respect to synthetic urine under normal pressure was 65.0 (g/g), and the water soluble component thereof was 7.2 percent by weight. Note that, it was found that the water soluble component of the polymer particles ($C_1$), due to the heat-treatment of 100° C. for 3 hours, has increased by substantially 2.7 percent by weight, compared with the case where no heat-treatment was carried out. Also, a first neutralization coefficient and a second neutralization coefficient of the polymer particles ($C_1$) were measured by the afore-described method. Note that, as comparative particles, crosslinked polyacrylic acids having a neutralization ratio of not more than 45 mole percent was adopted.

Then, with respect to 100 parts by weight of the polymer particles ($C_1$), 1 part by weight of propyleneglycol (first surface crosslinking agent), 0.05 part by weight of ethyleneglycol diglycidyl ether (second surface crosslinking agent), and an aqueous liquid (crosslinking solution) composed of 3 parts by weight of water and 2 parts by weight of isopropyl alcohol as a hydrophilic organic agent (total of 6.05 parts by weight) were added and mixed, and the mixture was subjected to heat-treatment of 185° C. for 20 minutes so as to carry out surface crosslinkage of the polymer particles ($C_1$), thus obtaining a water-absorbent agent. Various properties of the water-absorbent agent were measured by the afore-described method. Table 3 shows the results of the measurement along with the properties of the polymer particles ($C_1$).

EXAMPLE 6

The same static adiabatic polymerization as in Example 5 was carried out so as to obtain hydrogel polymer (D), except that the amount of N,N'-methylene-bisacrylamide (inner crosslinking agent) used is 513 mg (0.10 mole percent with respect to acrylic acid) rather than 769 mg.

After polymerization is finished, with respect to 1200 grams of unpulverized hydrogel polymer (D) having a maximum diameter of substantially 15 cm in the kneader, 208.2 grams of sodium hydroxide aqueous solution, 48 percent by weight, (75 mole percent with respect to acrylic acid) was added at a time (within 10 seconds) from the upper portion of the kneader. This resulted in a two-phase state in which an unabsorbed sodium hydroxide aqueous solution remained separately on the hydrogel polymer (D). Then, by rotating the blade of the kneader, a basic substance was added so as to neutralize and pulverize the unpulverized hydrogel polymer (D) simultaneously. As a result, the hydrogel polymer (D) was finely divided in substantially 10 minutes into irregular shaped particles, each having a diameter of not more than 10 mm, and no unabsorbed sodium hydroxide aqueous solution was observed with a naked eye. However, when 1 percent by weight of phenolphthalein-ethanol solution was directly added to the finely divided hydrogel polymer (D), a red purple color of phenolphthalein was still observed partially on the hydrogel polymer (D). When the blade was further rotated, the hydrogel polymer (D) was finely divided after 50 minutes into particles, each having a diameter of several mm (substantially 0.2 mm to 2 mm), and no red purple color of phenolphthalein was observed in each particle of the finely divided hydrogel polymer (D), and neutralization was finished. The neutralization ratio of hydrogel polymer after neutralization (referred to as neutralized gel ($D_1$) hereinafter) was 75 mole percent, and the solid content thereof was substantially 21 percent by weight.

Thereafter, the kneader was capped, and the neutralized gel ($D_1$) in the kneader was stirred in 30 rpm, and the temperature of the jacket was increased to 100° C. and the gel temperature was maintained at substantially 85° C. to 90° C., and while maintaining the solid content of 21 percent by weight, the neutralized gel ($D_1$) was subjected to heat-treatment for 3 hours. Then, the heat-treated neutralized gel ($D_1$) was taken out of the kneader, and was dried, pulverized, and classified in the same manner as in Example 5 so as to obtain, as a precursor of a water-absorbent agent, polymer particles (referred to as polymer particles ($D_1$)), each having a diameter of 300 $\mu$m to 600 $\mu$m. The water content of the polymer particles ($D_1$) was 8 percent by weight. The absorbency of the polymer particles ($D_1$) with respect to synthetic urine under normal pressure was 83.7 (g/g), and the water soluble component thereof was 18.1 percent by weight. Also, a first neutralization coefficient and a second neutralization coefficient of the polymer particles ($D_1$) were measured by the afore-described method.

Then, surface crosslinkage of the polymer particles ($D_1$) was carried out in the same manner as in Example 5 so as to obtain a water-absorbent agent. Various properties of the water-absorbent agent were measured by the afore-described method. Table 3 shows the results of the measurement along with the properties of the polymer particles ($D_1$).

EXAMPLE 7

In Example 5 and Example 6, the hydrogel polymer was finely divided after adding a base to an unpulverized integrated gel of the hydrogel polymer; however, the following describes an example wherein a base is added to hydrogel polymer which has already been finely divided so as to carry out neutralization.

Namely, in the present Example, the same polymerization and neutralization as in Example 6 were carried out, except that 208.2 grams (48 percent by weight) of sodium hydroxide aqueous solution (75 mole percent with respect to acrylic acid) was added while rotating the blade of the kneader after finely dividing the hydrogel polymer (D) into particles, each having a diameter of not more than 5 mm. As a result, the sodium hydroxide aqueous solution was quickly absorbed by the finely divided hydrogel polymer (D), and after 10 minutes, the red purple color of phenolphthalein was not observed anymore in each particle of the finely divided hydrogel polymer (D), and neutralization was finished.

Then, the hydrogel polymer after neutralization obtained by the described process was dried, pulverized, and classified in the same manner as in Example 6 so as to obtain, as a precursor of a water-absorbent agent, polymer particles (referred to as polymer particles ($D_2$)), each having a diameter of 300 µm to 600 µm. The water content of the polymer particles ($D_2$) was 7 percent by weight. Also, a first neutralization coefficient and a second neutralization coefficient of the polymer particles ($D_2$) were measured by the afore-described method.

Then, the same reactions and processes as in Example 6 (reactions and processes of Example 5) were carried out, except that the heating time for the mixture prepared by adding a crosslinking solution to the polymer particles ($D_2$) is 90 minutes, so as to obtain a water-absorbent agent through surface crosslinkage. Various properties of the water-absorbent agent were measured by the afore-described method. Table 3 shows the results of the measurement along with the properties of the polymer particles ($D_2$).

EXAMPLE 8

The same polymerization and neutralization as in Example 5 were carried out, except that the amount of 48 percent by weight of sodium hydroxide aqueous solution used for neutralization of the hydrogel polymer (C) is 194.3 grams (70 mole percent with respect to acrylic acid) instead of 180.4 grams. As a result, 50 minutes after the start of neutralization, the hydrogel polymer (C) was finely divided into particles, each having a diameter of several mm, and the red purple color of phenolphthalein was not observed anymore in each particle of the finely divided hydrogel polymer (C), and neutralization was finished. The neutralization ratio of hydrogel polymer after neutralization (referred to as neutralized gel ($C_2$) hereinafter) was 70 mole percent, and the solid content thereof was substantially 21 percent by weight.

Thereafter, the kneader was capped, and the neutralized gel ($C_2$) in the kneader was stirred in 30 rpm, and the temperature of the jacket was increased to 100° C. and the gel temperature of the neutralized gel ($C_2$) was maintained at substantially 85° C. to 90° C., and while controlling the solid content not to exceed about 24 percent by weight, the neutralized gel ($C_2$) was subjected to heat-treatment for 1.5 hours. Then, the heat-treated neutralized gel ($C_2$) was taken out of the kneader, and was dried, pulverized, and classified in the same manner as in Example 5 so as to obtain, as a precursor of a water-absorbent agent, polymer particles (referred to as polymer particles ($C_2$)), each having a diameter of 300 µm to 600 µm. The water content of the polymer particles ($C_2$) was 7 percent by weight. Also, a first neutralization coefficient and a second neutralization coefficient of the polymer particles ($C_2$) were measured by the afore-described method. Note that, as comparative particles, a crosslinked polyacrylic acid having a neutralization ratio of not more than 50 mole percent was adopted.

Then, the same reactions and processes as in Example 5 were carried out, except that the heating time for the mixture prepared by adding a crosslinking solution to the polymer particles ($C_2$) is 30 minutes, so as to obtain a water-absorbent agent through surface crosslinkage. Various properties of the water-absorbent agent were measured by the afore-described method. Table 3 shows the results of the measurement along with the properties of the polymer particles ($C_2$).

EXAMPLE 9

The same polymerization and neutralization as in Example 8 were carried out, except that the amount of N,N'-methylene-bisacrylamide (inner crosslinking agent) used is 667 mg (0.13 mole percent with respect to acrylic acid) instead of 769 mg, and that the base used for neutralization is 123.6 grams of sodium carbonate powder (70 mole percent with respect to acrylic acid) instead of 48 percent by weight of sodium hydroxide aqueous solution, so as to obtain neutralized hydrogel polymer (referred to as neutralized gel ($C_3$) hereinafter).

Thereafter, the kneader was capped, and the neutralized gel ($C_3$) in the kneader was stirred in 30 rpm, and the temperature of the jacket was increased to 100° C. and the gel temperature of the neutralized gel ($C_3$) was maintained at substantially 85° C. to 90° C., and while maintaining the solid content of the neutralized gel ($C_3$) at 24 percent by weight, the neutralized gel ($C_3$) was subjected to heat-treatment for 1 hour. Then, the heat-treated neutralized gel ($C_3$) was taken out of the kneader, and was dried, pulverized, and classified in the same manner as in Example 5 so as to obtain, as a precursor of a water-absorbent agent, polymer particles (referred to as polymer particles ($C_3$)), each having a diameter of 300 µm to 600 µm. The water content of the polymer particles ($C_3$) was 6 percent by weight. Also, a first neutralization coefficient and a second neutralization coefficient of the polymer particles ($C_3$) were measured by the afore-described method. Note that, as comparative particles, a crosslinked polyacrylic acid having a neutralization ratio of not more than 50 mole percent was adopted.

Then, the same reactions and processes as in Example 5 were carried out, except that the heating time for the mixture prepared by adding a crosslinking solution to the polymer particles ($C_3$) is 40 minutes, so as to obtain a water-absorbent agent through surface crosslinkage. Various properties of the water-absorbent agent were measured by the afore-described method. Table 3 shows the results of the measurement along with the properties of the polymer particles ($C_3$).

TABLE 3

|  | Examples | | | | |
| --- | --- | --- | --- | --- | --- |
|  | 5 | 6 | 7 | 8 | 9 |
| First Neutralization Coefficient | 2 | 1 | 1 | 1 | 1 |
| Second Neutralization Coefficient | 2 | 1 | 1 | 1 | 1 |
| Water-Soluble Component of Polymer particles (%) | 7.2 | 18.1 | 15.4 | 5.3 | 8.0 |
| Absorbency (g/g) of Polymer particles Under Normal Pressure | | | | | |
| Saline Solution | 48.2 | 66.5 | 57.2 | 51.0 | 47.8 |
| Synthetic Urine | 65.0 | 83.7 | 79.0 | 64.7 | 63.9 |
| Absorbency (g/g) of Water-Absorbent Agent Under Normal Pressure | | | | | |
| Saline Solution | 35.8 | 44.3 | 45.7 | 38.8 | 38.2 |
| Synthetic Solution | 50.3 | 54.2 | 53.4 | 48.5 | 47.6 |
| Absorbency (g/g) of Water-Absorbent Agent Under High Pressure | | | | | |
| Saline Solution | 30.0 | 29.1 | 26.5 | 28.7 | 30.0 |
| Synthetic Solution | 39.6 | 39.2 | 31.7 | 39.5 | 38.6 |
| Change in pH | <0.1 | <0.1 | <0.1 | <0.1 | <0.1 |

Comparative Example 4

The neutralized gel ($C_1$) (neutralization ratio of 65 mole percent) obtained through neutralization of hydrogel polymer (C) in Example 5 was dried by a hot air of 160° C. for 65 minutes without carrying out heat-treatment. Thereafter, as in Example 5, the dried product was dried, pulverized, and classified so as to obtain, as a precursor of a water-absorbent agent, comparative polymer particles (referred to as polymer particles ($C_1$)), each having a diameter of 300 μm to 600 μm. The water content of the polymer particles ($C_4$) was 8 percent by weight. Also, the absorbency of the polymer particles ($C_4$) with respect to synthetic urine under normal pressure was 65.0 (g/g), and the water soluble component thereof was 4.5 percent by weight. A first neutralization coefficient and a second neutralization coefficient of the polymer particles ($C_4$) were measured by the afore-described method. Note that, as comparative particles, a crosslinked sodium polyacrylic acid having a neutralization ratio of not more than 45 mole percent was adopted.

Then, the same reactions and processes as in Example 5 were carried out, except that the heating time for the mixture prepared by adding a crosslinking solution to the polymer particles ($C_4$) is 40 minutes, so as to obtain a water-absorbent agent through surface crosslinkage. various properties of the water-absorbent agent were measured by the afore-described method. Table 4 shows the results of the measurement along with the properties of the polymer particles ($C_4$).

Comparative Example 5

In the reaction vessel of Example 5, a reaction solution was prepared by dissolving 639 mg (0.03 mole percent with respect to acrylate) of polyethylene glycol diacrylate (inner crosslinking agent) in 1200 grams of partially neutralized sodium acrylate aqueous solution (33 percent by weight) with a neutralization ratio of 75 mole percent. Then, while maintaining the temperature of the reaction solution at 30° C., nitrogen replacement was carried out in the reaction vessel. Thereafter, while stirring the reaction solution by the blade of the kneader, 2.64 grams (20 percent by weight) of sodium persulfate aqueous solution (polymerization initializer) and 2.2 grams (1 percent by weight) of ascorbic acid aqueous solution were added, and resulting gel was chopped into small particles so as to carry out polymerization for 1 hour. As a result, particulate hydrogel crosslinked polymer (E) was obtained. The hydrogel crosslinked polymer (E) is a neutralized gel with a neutralization ratio of 75 mole percent, and no red purple color of phenolphthalein was observed after adding 1 percent by weight of phenolphthalein-ethanol solution. Note that, the average number of moles of ethylene oxide given to the polyethylene glycol diacrylate is 8 moles.

When it was confirmed that the coloration due to phenolphthaleinin was not observed in the hydrogel polymer (E), the hydrogel polymer (E) was directly placed in a drier without carrying out heat-treatment, and was dried, pulverized, and classified in the same manner as in Example 5 so as to obtain, as a precursor of a water-absorbent agent, comparative polymer particles (referred to as polymer particles ($E_1$)), each having a diameter of 300 μm to 600 μm. The water content of the polymer particles ($E_1$) was 6 percent by weight. The absorbency of the polymer particles ($E_1$) with respect to synthetic urine under normal pressure was 68.4 (g/g), and the water-soluble component thereof was 24.1 percent by weight. Also, a first neutralization coefficient and a second neutralization coefficient of the polymer particles ($E_1$) were measured by the afore-described method. Note that, as comparative particles, a crosslinked sodium polyacrylic acid having a neutralization ratio of not more than 55 mole percent was adopted.

Then, the same reactions and processes as in Example 5 were carried out, except that the heating time for the mixture prepared by adding a crosslinking solution to the polymer particles ($E_1$) is 40 minutes, so as to obtain a comparative water-absorbent agent through surface crosslinkage of the polymer particles ($E_1$). Various properties of the comparative water-absorbent agent were measured by the afore-described method. Table 4 shows the results of the measurement along with the properties of the polymer particles ($E_1$). Note that, the change in pH of the comparative water-absorbent agent was less than 0.1.

Comparative Example 6

In Example 5 through Example 9, a crosslinking agent is added to a polymerized powder after drying. In the present comparative example, a crosslinking agent is added to a neutralized gel before drying.

Namely, to the neutralized gel ($C_1$) in the kneader obtained in Example 5, with respect to 100 percent by weight of the solid component of the neutralized gel ($C_1$), 1 part by weight of propylene glycol (first surface crosslinking agent), 0.05 part by weight of ethyleneglycol diglycidyl ether (second surface crosslinking agent), and an aqueous liquid composed of 3 parts by weight of water and 2 parts by weight of isopropyl alcohol as a hydrophilic organic agent (total of 6.05 parts by weight) were added and mixed.

Thereafter, the kneader was capped, and the temperature of the jacket was increased to 100° C. After subjecting the neutralized gel ($C_1$) to heat-treatment for 1 hour without exceeding the solid component of 24 percent by weight, the neutralized gel ($C_1$) was dried, pulverized, and classified in the same manner as in Example 5 so as to obtain comparative water-absorbent agent (polymer particles), each having a diameter of 300 μm to 600 μm. The water content of the water-absorbent agent was 7 percent by weight. Also, various properties of the water-absorbent agent (polymer particles) were measured by the afore-described method. Table 4 shows the results of the measurement.

TABLE 4

|  | Comparative Examples | | |
|---|---|---|---|
|  | 4 | 5 | 6 |
| First Neutralization Coefficient | 16 | 0 | 1 |
| Second Neutralization Coefficient | 33 | 0 | 1 |
| Water-Soluble Component of Polymer particles (%) | 4.5 | 24.1 | 4.0 |
| Absorbency (g/g) of Polymer particles Under Normal Pressure | | | |
| Saline Solution | 48.0 | 49.7 | 38.0 |
| Synthetic Urine | 65.0 | 68.4 | 50.0 |
| Absorbency (g/g) of Water-Absorbent Agent Under Normal Pressure | | | |
| Saline Solution | 34.9 | 37.0 | 38.0 |
| Synthetic Solution | 49.3 | 45.0 | 50.0 |
| Absorbency (g/g) of Water-Absorbent Agent Under High Pressure | | | |
| Saline Solution | 17.0 | 23.1 | 7.6 |
| Synthetic Solution | 24.0 | 30.1 | 9.0 |

As it can be seen from the results in Table 3 and Table 4, as in Comparative Example 6, in the case where a crosslinking agent is not added to the polymerized powder after drying, absorbency under high pressure is significantly low. Also, it can be seen that the water-absorbent agents obtained in Example 5 through Example 9 have higher absorbency under high pressure than the water-absorbent agents obtained in Comparative Example 4 through Comparative Example 6. Therefore, in the present invention, high absorbency is realized not only under no applied pressure (normal pressure) but also under applied pressure, and the amount of water-soluble component is lowered compared with the water-absorbent agent produced by the conventional method (method in which neutralization is carried out before polymerization).

It can also be seen that compared with the polymer particles (Example 5 through Example 9 and Comparative Examples 4 and 6) obtained by post-neutralization, the polymer particles (Comparative Example 5) obtained by the method in which neutralization is carried out before polymerization contain more amount of water-soluble component (impurity). That is to say, even though the amount of water-soluble component in the polymer particles obtained in Example 5 through Example 9 is increased by the heat-treatment of a neutralized gel, the amount of water-soluble component is smaller compared with the polymer particles obtained by the method in which neutralization is carried out before polymerization.

Further, as it can also be seen from the results in Table 3, the polymer particles obtained in Examples 5 through 9 satisfy the requirements for the first neutralization ratio and the second neutralization ratio, and the sum of (a) the number of polymer particles having a first non-allowable neutralization ratio and (b) the number of polymer particles having a neutralization ratio of not less than 95 mole percent is not more than 10 in 200 polymer particles. Also, because the neutralization coefficient of the polymer particles during the crosslinking reaction is maintained in the water-absorbent agent as a final product, in the water-absorbent agents obtained in the present Examples, (1) the neutralization ratio of the water-absorbent agent particles constituting the water-absorbent agent is controlled, (2) neutralization is carried out uniformly at the particle level, (3) a change in pH with time while swelling is small, and (4) safety is superior.

The invention being thus described, it will be obvious that the same way may be varied in many ways. Such variations are not to be regarded as a departure from the spirit and scope of the invention, and all such modifications-as would be obvious to one skilled in the art are intended to be included within the scope of the following claims.

INDUSTRIAL APPLICATIONS OF THE PRESENT INVENTION

With the manufacturing method of a water-absorbent agent in accordance with the present invention, it is possible to stably provide a water-absorbent agent having high absorbency under no applied pressure as well as under high pressure wherein the amount of water soluble component is lower than that of a conventional water-absorbent agent. Also, when manufacturing the water-absorbent agent, by confirming beforehand conditions for satisfying the specified neutralization coefficient of the present invention, and by carrying out neutralization in accordance with the confirmed conditions, it is possible to efficiently obtain in a short period of time a water-absorbent agent having superior water absorbing characteristics.

Also, in the water-absorbent agent of the present invention, the neutralization ratio of the water-absorbent agent particles constituting the water-absorbent agent is controlled, and the neutralization is carried out uniformly at the particle level. For this reason, the water-absorbent agent of the present invention does not contain residual alkali and acid substances which are used for neutralization so that a change in pH with time is small even when the water-absorbent agent takes a form of a swollen gel by absorbing an aqueous liquid, and therefore the present water-absorbent agent is safe to use.

Thus, since the water-absorbent agent as obtained by the present invention efficiently exhibits the water absorbing ability even when adopted as a thin absorbent including a water-absorbent agent in high concentration, the present water-absorbent agent can be suitably adopted as an absorbent for thin sanitary articles employing a large amount of a water-absorbent agent.

What is claimed is:

1. A water-absorbent agent composed of water-absorbent agent particles obtained by post-neutralizing a hydrogel polymer produced by polymerizing a monomer component including an acid group containing unsaturated monomer (salt), wherein when an average neutralization ratio of the water-absorbent agent particles is $Z_2$ (mole percent), not less than 95 percent of the total number of water-absorbent agent particles have a neutralization ratio $Z_1$ which satisfies $Z_1 > Z_2 - 20$ (mole percent), and absorbency for a saline solution under a load of 50 g/cm$^2$ is not less than 20 g/g wherein the number of water-absorbent agent particles, in 200 particles of the water-absorbent agent particles, having a neutralization ratio by not less than 20 mole percent than the average neutralization ratio of the water-absorbent agent particles, is not more than 10 particles.

2. The water-absorbent agent as set forth in claim 1, wherein the neutralization ratio $Z_1$ of the water-absorbent agent particles exceeds 55 mole percent.

3. A water-absorbent agent composed of water absorbent agent particles obtained by post-neutralizing a hydrogel polymer produced by polymerizing a monomer component including an acid group containing unsaturated monomer (salt), wherein an average neutralization ratio of the water-absorbent agent particles is in a range of more than 30 mole percent and less than 95 mole percent, not less than 85 percent of the total number of water-absorbent agent particles have a neutralization ratio in a range of more than 30 mole percent and less than 95 mole percent, and absorbency for a saline solution under a load of 50 g/cm$^2$ is not less than 20 g/g wherein a sum of (a) water-absorbent agent particles having a neutralization ratio of not more than 30 mole percent and (b) water-absorbent agent particles having a neutralization ration of not less than 95 mole percent, respectively included in 200 particles of the water-absorbent agent particles, is not more than 30particles.

4. The water-absorbent agent as set forth in claim 1, wherein a change in pH after elapsed time of 5 minutes and after elapsed time of 120 minutes since swelling with water 100 times by a dead weight is not more than 0.2.

5. A water-absorbent agent, wherein a sum of (A) water-absorbent agent particles having a neutralization ratio of not more than 30 mole percent and (B) water-absorbent agent particles having a neutralization ration of not less than 95 mole percent, respectively included in 200 particles of the water-absorbent agent particlesin the water-absorbent agent, is in a range of not less than 1 and not more than 30.

6. The water-absorbent agent as set forth in claim 5, wherein absorbency for a saline solution under a load of 50 g/cm$^2$is not less than 20 g/g.

7. A method for manufacturing the water-absorbent agent of claim 1 composed of water-absorbent particles obtained by post-neutralizing a hydrogel polymer, the water-absorbent agent having an absorbency of not less than 20 g/g for a saline solution under a load of 50 g/cm$^2$, said method comprising the step of:

post-neutralizing the hydrogel polymer produced by polymerizing a monomer component including the acid group containing unsaturated monomer (salt), wherein a neutralization ratio of each of the polymer particles as a precursor of the water-absorbent agent obtained by post-neutralizing and thereafter drying and pulverizing the hydrogel polymer is controlled so that, when an average of the neutralization ratio of each of the polymer particles is $Z_2$ (mole percent), not less than 95 percent of the total number of water absorbent agent particles has a neutralization ratio $Z_1$ which satisfies:

$Z_1 > Z_2 - 20$(mole percent).

8. The method as set forth in claim 7, wherein said step of post-neutralization is controlled so that a first neutralization coefficient indicative of a number of polymer particles having a neutralization ratio lower, by not less than 20 mole percent, than the average neutralization ratio of the polymer particles, included in 20 particles of the polymer particles, is not more than 10.

9. The method as set forth in claim 8, wherein said post-neutralization is carried out until the first neutralization coefficient is not more than 5.

10. The method as set forth in claim 7, wherein the neutralization ratio lower by not less than 20 mole percent than the average neutralization ratio of the polymer particles is not more than 55 mole percent.

11. A method as set forth in claim 5 for manufacturing a water-absorbent agent, composed of water-absorbent agent particles obtained by post-neutralizing a hydrogel polymer, the water-absorbent agent having absorbency of not less than 20 g/g for a saline solution under a load of 50 g/cm$^2$, said method comprising the step of:

post-neutralizing the hydrogel polymer produced by polymerizing a monomer component including an acid group containing unsaturated monomer (salt), wherein the post-neutralization is controlled so that, in a predetermined quantity of the polymer particles as a precursor of the water-absorbent agent obtained by post-neutralizing and thereafter drying and pulverizing the hydrogel polymer, a proportion of polymer particles having a neutralization ratio of not more than 30 mole percent and those having a neutralization ratio of not less than 95 mole percent polymer particles is not more than 15 percent of the number of the polymer particles in the predetermined quantity.

12. The method as set forth in claim 11, wherein said step of post-neutralization is controlled a second neutralization coefficient indicative of a number of polymer particles having a neutralization ratio in a range of not more than 30 mole percent and not less than 95 mole percent, included in 200 particles of the polymer particles, is not more than 30.

13. The method as set forth in claim 12, wherein said post-neutralization is controlled so that the second neutralization coefficient is not more than 20.

14. The method as set forth in claim 7, wherein the acid group containing unsaturated monomer (salt) is a free acrylic acid.

15. The method as set forth in claim 7, wherein the polymer obtained by post-neutralizing the hydrogel polymer is allowed to react with a crosslinking agent which is reactive to a functional group of the polymer after adjusting a water content of the polymer to not more than 10 percent by weight.

16. The method as set forth in claim 7, wherein said post-neutralization is carried out by-adding an aqueous liquid after mixing the hydrogel polymer with a neutralizer.

17. The method as set forth in claim 16, wherein an amount of the aqueous liquid used with respect to 100 parts by weight of the hydrogel polymer is in a range of 5 parts by weight to 100 parts by weight.

18. A method for manufacturing a water absorbent agent of claim 1 or 3 composed of water-absorbent agent particles obtained by post-neutralizing a hydrogel polymer, the water-absorbent agent having an absorbency of not less than 20 g/g for a saline solution under a load of 50 g/cm$^2$, said method comprising the steps of:

(1) post-neutralizing the hydrogel polymer produced by polymerizing a monomer component including an acid group containing unsaturated monomer (salt);

(2) heat-treating the hydrogel polymer after post-neutralization for a period of time while maintaining a gel state;

(3) drying the heat-treated hydrogel polymer in a form of a powder; and (4) allowing the polymer obtained in said step (3) to react with a crosslinking agent which is reactive to a functional group of the polymer.

19. The method as set forth in claim 18, wherein said step (2) is carried out while maintaining a solid component of the hydrogel polymer in a range of 20 percent by weight to 40 percent by weight.

20. The method as set forth in claim 19, wherein said step (2) is carried out so that a change in concentration of a solid component of the hydrogel polymer is within ±30 percent by weight.

21. The method as set forth in claim 18, wherein said step (2) is carried out so that a charge in concentration of a solid component of the hydrogel polymer is within ±30 percent by weight.

22. The method as set forth in claim 18, wherein said step (2) is carried out until a water-soluble component of the polymer is increased by an amount in a range of 0.05 percent by weight to 20 percent by weight.

23. The method as set forth in claim 18, wherein said step (3) is carried out so that a solid component of the polymer is not less than 80 percent by weight.

24. The method as set forth in claim 18, wherein said step (1) is carried out simultaneously with pulverization of the hydrogel polymer.

25. The method as set forth in claim 18, wherein the hydrogel polymer prior to post-neutralization is in particle form and is obtained through static polymerization, and the hydrogel polymer particles have a maximum diameter of at least 1 cm.

26. The water-absorbent agent as set forth in claim 3, wherein a change in pH after elapsed time of 5 minutes and after elapsed time of 120 minutes since swelling with water 100 times by a deadweight is not more than 0.2.

27. The water-absorbent agent as set forth in claim 5, wherein a change in pH after elapsed time of 5 minutes and after elapsed time of 120 minutes since swelling with water 100 times by a dead weight is not more than 0.2.

28. The water-absorbent agent as set forth in claim 1, wherein the hydrogel polymer is included inside a crosslinking structure introduced by an inner crosslinking agent, and the inner crosslinking agent is an inner crosslinking agent with no ester bond.

29. The water-absorbent agent as set forth in claim 3, wherein the hydrogel polymer is included inside a crosslinking structure introduced by an inner crosslinking agent, and the inner crosslinking agent is an inner crosslinking agent with no ester bond.

30. The water-absorbent agent as set forth in claim 5, wherein the hydrogel polymer is included inside a crosslinking structure introduced by an inner crosslinking agent, and the inner crosslinking agent is an inner crosslinking agent with no ester bond.

31. The water-absorbent agent as set forth in claim 1, wherein a temperature when adding a neutralizer to the hydrogel polymer is maintained in a range of 40° C. to 100° C., and a temperature after the neutralizer is added is maintained in a range of 0° C. to 80° C.

32. The water-absorbent agent as set forth in claim 3, wherein a temperature when adding a neutralizer to the hydrogel polymer is maintained in a range of 40° C. to 100° C., and a temperature after the neutralizer is added is maintained in a range of 0° C. to 80° C.

33. The water-absorbent agent as set forth in claim 5, wherein a temperature when adding a neutralizer to the hydrogel polymer is maintained in a range of 40° C. to 100° C., and a temperature after the neutralizer is added is maintained in a range of 0° C. to 80° C.

34. The method as set forth in claim 11, wherein the acid group containing unsaturated monomer (salt) is a free acrylic acid.

35. The method as set forth in claim 11, wherein the polymer obtained by post-neutralizing the hydrogel polymer is allowed to react with a crosslinking agent which is reactive to a functional group of the polymer after adjusting a water content of the polymer to not more than 10 percent by weight.

36. The method as set forth in claim 11, wherein said post-neutralization is carried out by adding an aqueous liquid after mixing the hydrogel polymer with a neutralizer.

37. The method as set forth in claim 36, wherein an amount of the aqueous liquid used with respect to 100 parts by weight of the hydrogen polymer is in a range of 5 parts by weight to 100 parts by weight.

* * * * *